US006736790B2

(12) United States Patent
Barbut et al.

(10) Patent No.: US 6,736,790 B2
(45) Date of Patent: May 18, 2004

(54) METHOD AND SYSTEM FOR SELECTIVE OR ISOLATED INTEGRATE CEREBRAL PERFUSION AND COOLING

(76) Inventors: Denise R. Barbut, 70 E. 77th St., New York, NY (US) 10021; Russel H. Patterson, 146 W. 57th St., New York, NY (US) 10019

( * ) Notice: Subject to any disclaimer, the term of this patent is extended or adjusted under 35 U.S.C. 154(b) by 53 days.

(21) Appl. No.: 09/904,016

(22) Filed: Jul. 11, 2001

(65) Prior Publication Data

US 2001/0038807 A1 Nov. 8, 2001

Related U.S. Application Data

(63) Continuation of application No. 09/256,965, filed on Feb. 24, 1999, now abandoned.
(60) Provisional application No. 60/076,222, filed on Feb. 25, 1998, and provisional application No. 60/096,218, filed on Aug. 12, 1998.

(51) Int. Cl.[7] .................. A61M 37/00; A61M 1/00; A61M 29/00; A61B 1/267; A61F 7/12
(52) U.S. Cl. .................. 604/6.13; 604/4.01; 604/6.16; 604/6.14; 604/28; 604/509; 604/96.01; 604/101.04; 604/113; 600/194; 607/106
(58) Field of Search .................. 422/44, 45, 61; 604/4.01, 6.01, 6.13, 6.14, 8, 19, 27, 28, 500, 506–509, 113, 164.11, 96.01, 98.01, 101.04, 102.01–102.03, 104, 907, 912, 915, 919, 921; 435/1.1, 1.2, 2, 284.1, 283.1; 128/898, DIG. 13, DIG. 12, DIG. 27, DIG. 913; 261/DIG. 28; 606/191–195, 198, 200; 607/96, 104–106

(56) References Cited

U.S. PATENT DOCUMENTS 2,876,769 A    3/1959   Cordova
3,881,483 A    5/1975   Sausse
4,198,963 A    4/1980   Barkalow et al.
4,416,280 A   11/1983   Carpenter et al.
4,450,841 A    5/1984   Osterholm
4,459,977 A    7/1984   Pizon et al.
4,540,399 A    9/1985   Litzie
4,666,425 A    5/1987   Fleming
4,850,969 A    7/1989   Jackson
4,917,667 A    4/1990   Jackson
5,011,469 A    4/1991   Buckberg et al.

(List continued on next page.)

FOREIGN PATENT DOCUMENTS

WO     WO 00/74749     12/2000

OTHER PUBLICATIONS

Cassak, "Cool is Hot: The Promise of Hypothermia," *Medical Devices' Ice Age* from In Vivo Jan. 2001.

(List continued on next page.)

*Primary Examiner*—Patricia M. Bianco
(74) *Attorney, Agent, or Firm*—O'Melveny & Myers LLP

(57) ABSTRACT

Patients having diminished circulation in the cerebral vasculature as a result of cardiac arrest or from other causes are treated by flowing an oxygenated medium through an arterial access site into the cerebral vasculature and collecting the medium through an access site in the venous site of the cerebral vasculature. In addition to oxygenation, the recirculating blood may also be cooled to hypothermically treat and preserve brain tissue. Isolation and cooling of cerebral vasculature in patients undergoing aortic and other procedures is achieved by internally occluding at least the right common carotid artery above the aortic arch. Blood or other oxygenated medium is perfused through the occluded common carotid artery(ies) and into the arterial cerebral vasculature. Usually, oxygen depleted blood or other medium leaving the cerebral vasculature is collected, oxygenated, and cooled in an extracorporeal circuit so that it may be returned to the patient.

10 Claims, 15 Drawing Sheets

U.S. PATENT DOCUMENTS

| | | | |
|---|---|---|---|
| 5,066,578 A | | 11/1991 | Wilkman-Coffelt |
| 5,084,011 A | | 1/1992 | Grady |
| 5,149,321 A | | 9/1992 | Klatz et al. |
| 5,188,107 A | | 2/1993 | Omura |
| 5,195,976 A | | 3/1993 | Swenson |
| 5,216,032 A | | 6/1993 | Manning |
| 5,234,405 A | | 8/1993 | Klatz et al. |
| 5,308,320 A | | 5/1994 | Safar et al. |
| 5,334,142 A | | 8/1994 | Paradis |
| 5,383,854 A | | 1/1995 | Safar et al. |
| 5,395,314 A | | 3/1995 | Klatz et al. |
| 5,437,633 A | | 8/1995 | Manning |
| 5,531,776 A | | 7/1996 | Ward et al. |
| 5,584,804 A | | 12/1996 | Klatz et al. |
| 5,626,143 A | | 5/1997 | Meyer, III |
| 5,653,685 A | | 8/1997 | Klatz et al. |
| 5,792,094 A | * | 8/1998 | Stevens et al. ............ 604/4.01 |
| 5,827,222 A | | 10/1998 | Klatz et al. |
| 5,843,024 A | | 12/1998 | Brasile |
| 5,989,238 A | | 11/1999 | Ginsburg |
| 6,042,559 A | | 3/2000 | Dobak, III |
| 6,096,068 A | | 8/2000 | Dobak, III |
| 6,110,139 A | | 8/2000 | Loubser |
| 6,110,145 A | * | 8/2000 | Macoviak .............. 604/101.01 |
| 6,117,105 A | | 9/2000 | Bresnaham et al. |
| 6,139,517 A | | 10/2000 | Macoviak et al. |
| 6,161,547 A | * | 12/2000 | Barbut ....................... 128/898 |
| 6,165,162 A | | 12/2000 | Safar et al. |
| 6,295,990 B1 | * | 10/2001 | Lewis et al. ................ 128/898 |
| 6,379,331 B2 | * | 4/2002 | Barbut et al. ............... 604/113 |
| 6,383,172 B1 | * | 5/2002 | Barbut ....................... 604/509 |
| 6,398,752 B1 | * | 6/2002 | Sweezer et al. ........... 604/6.14 |
| 6,436,071 B1 | * | 8/2002 | Schwartz .................... 604/113 |
| 6,478,186 B1 | * | 11/2002 | Willach et al. ............... 221/13 |

OTHER PUBLICATIONS

Jikuya et al., "Species Differences in Erythrocyte Mechanical Fragility," *ASAIO Journal* 44:M452–M455 (1998).

Kawahito et al., "Hemolysis in Different Centrifugal Pumps," *Artificial Organs,* 21(4):323–326 (1997).

Kirkeby et al., "Intracerebral laser Doppler blood flow measurements compared to blood flow in porcine internal carotid artery," *Journal of Clinical Neuroscience* 6(5):389–394 (1999).

Meadow et al., "Correlation of Flow Probe Determinations of Common Carotid Artery Blood Flow and Internal Carotid Artery Blood Flow with Microsphere Determinations of Cerebral Blood Flow in Piglets," *Pediatrics Research* 45(3):324–330 (1999).

Parkins et al., "Brain cooling in the prevention of brain damage during periods of circulatory occlusion in dogs," *Annals of Surgery* 140(3):284–289(1954).

Schwartz et al., "Isolated Cerebral Hypothermia by Single Carotid Artery Perfusion of Extracorporeally Cooled Blood in Baboons," *Neurosurgery* 39(3):577–579 (1996).

Schwartz et al., "Selective Cerebral Hypothermia by Means of Transfemoral Internal Carotid Artery Catheterization," *Radiology* 201(2):571–572 (1996).

Tamagawa et al., "Prediction of Hemolysis in Turbulent Shear Orifice Flow," *Artificial Organs* 20(6):553–559 (1996).

Van Meurs et al., "Maximum Blood Flow Rates for Arterial Cannulae Used in Neonatal ECMO," *ASAIO Transactions* 36:M679–M681 (1990).

Kazui et al., "Selective Cerebral Perfusion During Operation for Aneurysms of the Aortic Arch: A Reassessment," *The Annals of Thoracic Surgery*, Jan. 1992, 53:109–114, Elsevier Science Publishing Co., Inc., New York.

Manning et al., "Selective Aortic Arch Perfusion During Cardiac Arrest: A New Resuscitation Technique," *Annals of Emergency Medicine*, Sep. 1992, 21:1058–1065, Journal of the American College of Emergency Physicians and the Society for Academic Emergency Medicine, USA.

Mohri et al., "Protection of the Brain During Hypothermic Perfusion," *The Annals of Thoracic Surgery*, Dec. 1993, 56:1493–1496, Elsevier Science Publishing Co., Inc., New York.

Safar, "Cerebral Resuscitation After Cardiac Arrest: Research Initiatives and Future Directions," *Annals of Emergency Medicine*, Feb. 1993, 22:324–349, Journal of the American College of Emergency Physicians and the Society for Academic Emergency Medicine, USA.

Tanaka et al., "Experimental Study on the Optimum Flow Rate and Pressure for Selective Cerebral Perfusion," *The Annals of Thoracic Surgery*, Mar. 1995, 59:651–657, Elsevier Science Publishing Co., Inc., New York.

Tucker et al., "Advanced Cardiac Life Support: Update on Recent Guidelines and a Look at the Future," *Clinical Cardiology*, Sep. 1995, 18:497–504, Foundation for Advances in Medicine and Science, Inc., USA.

* cited by examiner

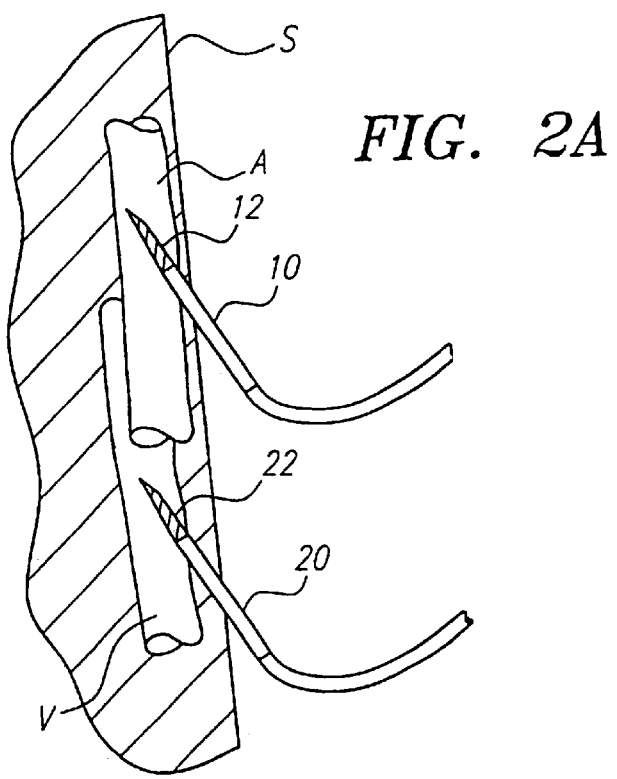
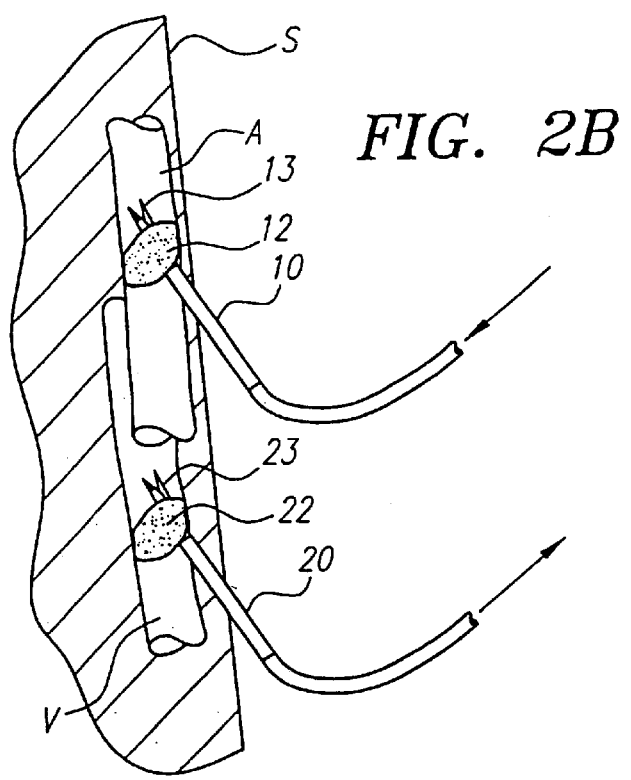

METHOD AND SYSTEM FOR SELECTIVE OR ISOLATED INTEGRATE CEREBRAL PERFUSION AND COOLING

This is a continuation of Barbut et al., U.S. application Ser. No. 09/256,965, filed Feb. 24, 1999, now abandoned, which is a continuation-in-part of Barbut et al., U.S. application Ser. No. 60/076,222, filed Feb. 25, 1998, entitled "Method and System for Emergency Cerebral Perfusion," and a continuation-in-part of U.S. application Ser. No. 60/096,218, filed Aug. 12, 1998, entitled "Methods and Apparatus for Isolation of the Cerebral Vasculature." All of the above-identified applications are expressly incorporated herein by reference in their entirety.

FIELD OF THE INVENTION

The present invention relates generally to medical devices and methods. More particularly, the present invention relates generally to methods, systems, and kits for perfusing and optionally cooling the cerebral vasculature of a patient with oxygenated blood or other media.

Cerebral ischemia, i.e., reduction or cessation of blood flow to the cerebral tissue, can be characterized as either focal or global. Focal cerebral ischemia refers to reduced perfusion to the cerebral tissue resulting from a partial or complete occlusion in the intracranial or extracranial cerebral arteries, e.g., stroke, subarachnoid hemorrhage spasms, iatrogenic vasospasm. Global cerebral ischemia refers to reduced perfusion to the cerebral tissue resulting from systemic circulatory failure caused by, e.g., cardiac arrest, shock, circulatory arrest, and septicemia.

Cardiac arrest is a major contributor to global cerebral ischemia. Cardiac arrest refers to cessation or significant reduction of a patient's cardiac output and effective circulation to vital organs, most importantly the brain. Cardiac arrest can result from a number of causes, such as electrical dysfunction, mechanical failure, circulatory shock, or an abnormality in ventilation. Within minutes of blood flow cessation, tissue becomes ischemic (oxygen deprived), particularly in the heart and brain. Brain tissue is perhaps most immediately at risk, with severe, irreversible damage occurring minutes after the initial cardiac arrest. Patients in cardiac or circulatory arrest are usually treated by a combination of forced ventilation of the lungs and forced compression of the heart. Most commonly, cardiopulmonary resuscitation (CPR) is applied to the patient, with manual chest compression and mouth-to-mouth resuscitation. Advanced cardiac support (ACS) may also be provided in the form of drugs, defibrillation, and other techniques. Less commonly, open chest massage of the heart may be performed, particularly in a hospital setting where skilled surgeons may be present. Open chest heart massage is probably the most effective technique at resuscitating a patient and avoiding ischemic brain damage, but the technique is quite invasive and not available in most emergency situations.

CPR and other techniques which are directed at mechanical heart compression and lung ventilation do not usually provide adequate brain oxygenation. In addition, vasoconstrictors, e.g., epinephrine, administered during CPR are often either ineffective or given in dosages too high to produce systemic blood pressure required for cerebral perfusion. In the best cases, conventional cardiac resuscitation techniques will provide no more than 1 l/min of total blood circulation (with only about 200 ml/min passing through the cerebral vasculature) and no more than 5 to 15 mmHg of blood pressure. Normal circulation and blood pressure are 5 l/min and 80 to 100 mmHg, respectively, with about 1 l/min passing through the cerebral vasculature. Such flows are usually not adequate at normothermia. Even when CPR techniques are applied within the first several minutes of a cardiac arrest, the percentage of patients who survive without significant brain damage is very low. Significantly, most patients suffering from cardiac arrest die because of cerebral hypoperfusion.

Recognizing such problems, alternative techniques for treating patients in cardiac arrest have been proposed. Of particular interest to the present invention, the emergency use of cardiopulmonary bypass machines for supporting and cooling systemic circulation has been proposed. Generally, access is provided with a pair of catheters, where one of the catheters may be balloon-tipped to partition the circulation and permit the desired bypass. While such systems are theoretically effective, they do not isolate the cerebral vasculature and do not necessarily provide sufficient oxygenation of the brain. Moreover, the need to deploy intravascular catheters is time consuming and must be performed by a highly skilled and trained personnel.

Surgical procedures on the aorta are required for the treatment of a number of conditions, such as aortic aneurysms, occlusional diseases, aortic dissection, and the like. Exemplary procedures include conventional aortic aneurysm repair and grafting, endarterectomy for the treatment of aortic atheroma, stenting for the treatment of aortic atheroma or dissection, and the like. Such procedures frequently require that the aorta be surgically opened to permit reconstruction or other surgical modification. Surgically accessing and opening the aorta will usually further require that the patient's circulation be arrested, i.e., blood flow through the aorta cannot be accommodated while the aorta is being surgically accessed. Cessation of systemic circulation places a patient at great risk, particularly in the cerebral vasculature where ischemia can rapidly lead to irreversible brain damage.

A number of techniques have been proposed to at least partially protect a patient having arrested circulation during a variety of aortic procedures. It will be appreciated that conventional cardiopulmonary bypass (CABG) techniques will generally not be useful when the aorta does not remain in tact. Thus, various alternative protective protocols have been proposed.

"Retrograde aortic perfusion (RAP) can be used when a procedure is being performed on the aorta between the heart and the aortic arch. The aorta is clamped beneath the aortic arch and retrograde aortic perfusion established, typically via femoral access. Advantageously, such retrograde perfusion can continue throughout the procedure since the operative site within the aorta is isolated by the clamp. RAP, however, is disadvantageous in a number of respects. In particular, retrograde perfusion often results in significant cerebral embolization from dislodgment of atheromatous material in the descending aorta and aortic arch. Such risk, as well as the limited region of the aorta that can be operated on, makes RAP less than ideal. Moreover, RAP is not useful for procedures distal or proximal to the isolated region of the aorta and is useful only at the beginning of procedures performed within the isolated aortic region".

Another approach for protecting the brain during aortic arch procedures is referred to as hypothermic circulatory arrest (HCA). HCA relies on inducing marked hypothermia in the entire body prior to stopping blood circulation altogether. Circulation remains stopped during the entire aortic procedure, thus placing the patient at significant risk of ischemia (despite the hypothermia). The patient is at further risk because the whole body has been cooled, thus increasing the duration of the surgery to accommodate the time needed to return to normal body temperature. HCA has also been associated with systemic coagulopathy (impaired coagulation) in a significant number of patients. Coagulopathy can require blood and plasma transfusion, both of which have been associated with the risk of viral infection. Aortic surgery performed with HCA has a very high morbidity, typically about 20%.

In order to retain some cerebral circulation during the time the aortic arch is accessed, HCA may be combined with retrograde cerebral venous perfusion (RCP). A catheter is placed in the superior vena cava and oxygenated blood introduced. Flow is established in a retrograde direction up the vena cava into the brachial and jugular veins. Unfortunately, very little of the oxygenated blood will reach the cerebral vessels for a number of reasons. For example, as much as 85% of the blood will enter the brachial veins and go to the arms with as little as 205 of the blood entering the brain. Moreover, the jugular venous valves may inhibit the blood from reaching the cerebral vessels. Blood that does reach the cerebral veins immediately flows outwardly through the extensive collateral circulation without perfusing the brain tissue. The amount of blood that returns to the aorta from the carotid arteries represents no more than about 5% of the total blood that is initially introduced to the superior vena cava. Additionally, as observed by the inventor herein, such retrograde perfusion results in a build up of the cerebral pressure that further inhibits any blood inflow. For these reasons, HCA, even when combined with RCP, falls far short of providing adequate protection for the patient during procedures performed on the aorta.

Another procedure for perfusing the brain during aortic procedures has recently been proposed. The procedure is referred to as selective antegrade cerebral perfusion (SCP) and relies on introducing a catheter through the aorta into a carotid artery in order to perfuse the cerebral vasculature. Introduction of the catheter can dislodge atheromatous material which will often be present at the take-off from the aorta and which may thus cause cerebral embolization. Furthermore, in order to prevent air from entering the cerebral vessels, the carotid artery and all other cerebral arteries must be externally clamped or snared, which can cause atheromatous embolization. While the procedure can more effectively maintain cerebral perfusion than HCP, alone or combined with RCP, the risk of both air and atheromatous embolization more than outweighs any associated benefits from enhanced perfusion.

It would therefore be desirable to provide improved methods and systems for perfusing the cerebral vasculature of a patient suffering from either focal or global cerebral ischemia with oxygenated blood or other media in patients. Such methods and systems should be suitable for rapid deployment, be capable of use outside of a hospital environment, and should be capable of being performed with less skilled personnel than comparable catheter-based systems. Preferably, such systems may be deployed via direct percutaneous cannulation of the patient vasculature. In addition, the method and systems of the present invention should be suitable for use with patients undergoing cardiac and vascular procedures where it is desirable to perfuse and/or isolate the cerebral vasculature. At least some of these objectives will be met by the invention of the present application.

For these reasons, it would be desirable to provide improved methods, systems, and kits for protecting the brain and cerebral vasculature during the performance of surgical procedures on the aorta. In particular, it would be desirable to provide for cerebral perfusion which is both antegrade and continuous throughout performance of the aortic procedure and which would enable profound cerebral hypothermia without systemic hypothermia. It would be further desirable to provide for improved isolation of the cerebral vasculature, still more preferably with minimum and ideally no external clamping. It would be still further desirable to minimize the risk of air and/or atheromatous embolization in the cerebral vasculature or elsewhere as a result of the aortic procedure. Such methods, systems, and kits should be compatible with reduced and/or localized hypothermia, particularly hypothermia directed specifically at the cerebral vasculature. In addition, cerebral isolation, perfusion and cooling should be compatible with systems and methods for perfusing non-cerebral portions of the patient's vasculature. At least some of these objectives will be met by the invention described hereinafter.

DESCRIPTION OF THE BACKGROUND ART

Selective cerebral perfusion (SCP) procedures are described in Kazui et al. (1992) *Ann. Thorac. Surg.* 53:109–114; Mohri et al. (1993) *Ann. Thorac. Surg.* 56:1493–1496; and Tanaka et al. (1995) *Ann. Thorac. Surg.* 59:651–657. Advanced cardiac life support techniques are discussed and compared in Tucker et al. (1995) *Clin. Cardiol.* 18:497–504. Emergency cardiopulmonary bypass using access needles introduced via a cut-down procedure is described in Litzie, U.S. Pat. No. 4,540,399. Emergency cardiopulmonary bypass using catheter-based access is described in Safar et al., U.S. Pat. No. 5,383,854; Safar et al., U.S. Pat. No. 5,308,320; Buckberg et al., U.S. Pat. No. 5,011,469; and Safar (1993) *Ann. Emerg. Med.* 22:58/324–83/349. A cardiopulmonary bypass system with cooling having a balloon tipped cannula for accessing the inferior vena cava and an anastomotically attached catheter for accessing the femoral artery is described in Sausse, U.S. Pat. No. 3,881,483. Cerebral infusion with cooled and/or preservative media is described in Klatz et al., U.S. Pat. Nos. 5,149,321; 5,234,405; 5,395,314; 5,584,804; and 5,653,685. Aortic perfusion with balloon catheters is described in Paradis, U.S. Pat. No. 5,334,142; Manning, U.S. Pat. No. 5,437,633; and Manning et al. (1992) *Ann. Emerg. Med.* 21:28–35. Coronary and/or cerebral retroperfusion is described in Pizon et al., U.S. Pat. No. 4,459,977; Jackson, U.S. Pat. No. 4,850,969; Jackson, U.S. Pat. No. 4,917,667; and Grady, U.S. Pat. No. 5,084,011. Other relevant patents include Barkalow et al., U.S. Pat. No. 4,198,963; Ward et al., U.S. Pat. No. 5,531,776; and Meyer, III, U.S. Pat. No. 5,626,143.

SUMMARY OF THE INVENTION

According to the present invention, methods, systems, and kits are provided for perfusing an oxygenated medium, usually autologous blood, through the cerebral vasculature of patients suffering from global ischemia caused by, e.g., cardiac arrest, shock, circulatory arrest, and septicemia; focal ischemia caused by stroke, subarachnoid hemorrhage spasms, iatrogenic vasospasm; or, cerebral edema, e.g., head trauma. The method, systems, and kits are useful not only in providing selective isolated cerebral perfusion during all conditions of cerebral ischemia, but also in reducing the dosage of vasoconstrictors required to achieve a desired perfusion pressure.

Optionally, in addition to improving cerebral perfuision, the methods of the present invention may combine or otherwise rely on cooling of the patient's head and cerebral vasculature in treatment of both global and focal cerebral ischemia to inhibit tissue damage resulting from lack or limitation of cerebral blood circulation. Usually, the oxygenated medium which is circulated as part of the methods of the present invention will be cooled in order to cool the brain tissue and reduce the risk of ischemic damage. Further optionally, the patient's head may be cooled even prior to initiating perfusion of externally oxygenated, optionally cooled blood. In some instances, the cooled blood can be used to externally cool the patient's head during the treatment protocol, e.g., by passing the blood through a helmet or other structure which permits the blood to selectively cool the head. This selective isolated cooling of the head and/or cerebral vasculature is desirable and preferred over systemic cooling, since coagulopathy, poor healing, cardiac arrhythmia and cardiac arrest can ensue as a result of systemic cooling.

The methods of the present invention for improving cerebral perfusion comprise accessing at least one extracranial vein, such as the internal jugular vein, the femoral vein, and/or the subelavian vein, and accessing at least one artery which feeds the cerebral vasculature through incisions on any extracranial artery, such as the common carotid artery, the internal carotid artery, the femoral artery, or the subclavian artery. In providing both selective isolated perfusion and cooling of the cerebral tissue, the methods comprise assessing at least one thing at location(s) which drain at least a portion of the cerebral vasculature, such as the internal jugular vein and/or external jugular vein, and assessing at least one artery which feeds the cerebral vasculature through incisions on any extracranial artery, such as the common carotid artery, the internal carotid artery, the femoral artery, or the subdlavian artery. In emergency cases, access will usually be provided by a percutaneous needle stick as described in more detail below. When performed in conjunction with aortic arch or other cardiac surgery, in contrast, the access will usually be provided via surgical exposure of the target vein(s) and artery(ies). An oxygenated medium is flowed from the arterial access location through the cerebral vasculature to the venous access location in order to perfuse the cerebral vasculature with the oxygenated medium. The vein(s) and artery(ies) are chosen to provide access to at least a major portion of the blood circulation through the cerebral vasculature. Preferably, the vein(s) and artery(ies) will also be directly accessible via a percutaneously inserted needle or other cannula for emergency performance of the procedures in the field. Suitable veins include the internal and/or external jugular vein, the superior vena cava, and the like. Suitable arteries include the common carotid arteries, the external and internal carotid artery, and the like. The particular access sites in each of the artery and vein will be selected based primarily on percutaneous accessibility. Preferred venous access sites lie within the internal jugular vein and preferred venous access sites lie within the common carotid artery.

After access is established, typically using percutaneously introduced needles, cannulas, or other conduits, a flow of oxygenated medium is initiated at a rate sufficient to provide oxygen to the brain tissue. The rate will depend on the amount of oxygen being carried by the oxygenated medium, typically being in the range from 0.1 l/min to 1.5 l/min, typically from 0.2 l/min to 1 l/min. For oxygenated autologous blood, the rate will typically be in the range from 0.2 l/min to 1 l/min. In some instances, in order to inhibit possible reperfusion injury, it will be desirable to initiate the flow rate of oxygenated medium at a relatively low rate and subsequently increase the flow rate to a final rate within the ranges set forth above. Usually, the final flow will be maintained at a steady rate, but it will also be possible to initiate a pulsatile or other nonsteady flow rate.

In order to enhance the efficiency of oxygenated medium delivered to the cerebral vasculature, it will usually be desirable to at least partly occlude the access blood vessel(s) near the access sites in order to prevent flow away from the cerebral vasculature. That is, at the venous access site(s), the vein will be occluded in order to inhibit flow caudal to the access location. At the arterial access site(s), the artery will be occluded to inhibit flow into the aorta. As described in more detail in connection with the systems of the present invention, such occlusion will typically be provided by inflatable occluding balloons on the access needles, cannulas, or other conduits.

In the preferred methods of the present invention, the oxygenated medium will consist essentially of blood, usually patient autologous blood, and the blood will be recirculated from the venous access location to the arterial access location using a pump. In addition to the primary antegrade flow, some flow may occur in a retrograde direction to the contralateral hemisphere and/or posterior territories as well. The blood will be extracorporeally oxygenated and optionally cooled, typically to a temperature in the range from 7° C. to 35° C. External pumping, oxygenation, and cooling can be provided by systems of a type used for cardiopulmonary bypass procedures.

Alternatively, the oxygenated medium may comprise a synthetic oxygen carrier, such as a perfluorocarbon, or other synthetic blood substitute material. In some instances, such synthetic oxygen carriers may be combined with patient or non-autologous blood. The synthetic oxygen carriers may be preoxygenated and flowed through the cerebral vasculature only once. In such cases, a large reservoir of the synthetic oxygen carrier may be provided, passed through the cerebral vasculature, and collected as it passes out of the venous access site. Alternatively, the synthetic oxygen medium, optionally combined with blood, may be extracorporally recirculated and oxygenated as described above for autologous blood.

In all cases, the oxygenated medium may have other biologically active agents combined therewith. For example, drugs and biological agents which inhibit deterioration of brain tissue in cases of limited oxygen supply may be utilized. Such compositions include NMDA receptor-inhibitors, calcium-channel blockers, anticoagulants, glutamate inhibitors, free-radical inhibitors, vasodilators, and the like.

The present invention still further provides improved methods for selective isolated cerebral perfusion in patients with global or focal ischemia. Such improved methods comprise isolating at least a portion of the patient's cerebral vasculature from the remainder of patient circulation, typically by partitioning using occlusion balloons as described in more detail hereinafter. Patient blood is oxygenated and recirculated through the isolated vasculature in order to inhibit ischemia and resulting damage to brain tissue while steps are taken to treat the cardiac arrest.

In yet another aspect of the method of the present invention, improved antegrade cerebral perfusion with an oxygenated medium comprises introducing the oxygenated medium, typically autologous blood, to a carotid artery to establish antegrade flow into the cerebral vasculature. The oxygenated medium, after it has passed through the cerebral vasculature, is collected through a jugular vein. Such improved methods may be used with both once-through perfusion using a synthetic oxygen carrier and/or heterologous oxygenated blood. More usually, such improved methods will be used with extracorporeal recirculation and oxygenation of autologous blood.

Systems according to the present invention for recirculating and oxygenating blood in the cerebral vasculature of a patient comprise a venous cannula, an arterial cannula, a pump, and an oxygenator. The venous cannula typically has a lumen diameter in the range from 2 mm to 4 mm and includes a distal occlusion balloon, wherein the cannula and balloon are sized to access and occlude a vein which drains the cerebral vasculature, typically a jugular vein. The arterial cannula typically has a lumen diameter in the range from 2 mm to 4 mm and also has a distal occlusion balloon, and the cannula and balloon are sized to access and occlude an artery which feeds the cerebral vascular, typically the common carotid artery. The pump may be connected between the venous cannula and the arterial cannula to circulate blood from the venous cannula to the arterial cannula, typically at a flow rate in the ranges set forth above. The oxygenator processes the externally circulating blood to provide a desired degree of oxygenation, also within the ranges set forth above.

The present invention still further provides kits including a venous cannula sized to access a vein which drains the cerebral vasculature and an arterial cannula sized to access an artery which feeds the cerebral vasculature. Such kits will further include instructions for use according to any of the methods set forth above. Additionally, the kits may comprise a package for holding all or a portion of the kit components, typically in a sterile condition. Typical packages include trays, pouches, boxes, tubes, and the like. Preferably, the cannulas will each have an occlusion balloon sized to occlude the respective blood vessel lumen into which they are placed. Other optional kit components include oxygenated medium, drugs to be delivered via the flowing blood or other oxygenated medium, catheters for connecting the cannulas to an extracorporeal recirculation/oxygenation cooling system, cassettes for use with such extracorporeal recirculation systems, cooling elements, thermometers, pressure transducers, and the like.

In still other embodiments, methods, systems, and kits are provided for isolating and perfusing the cerebral vasculature, usually to facilitate access to a patient's aorta, during performance of a diagnostic or interventional procedure on the aorta, more usually during performance of an open surgical interventional procedure on the aorta, such as repair of an aortic aneurysm, dissections, reconstruction of the aorta, endarterectomy, or the like. The heart will usually be arrested during open surgical procedures where the aorta is opened and procedure is performed within the lumen of the aorta. In some instances, however, the heart may remain beating while the procedure is performed intravascularly, i.e. through using catheters and other instruments introduced from the peripheral vasculature and into the aorta. The methods of the present invention will serve primarily to isolate the cerebral vasculature and prevent gaseous and atheromatous emboli from entering the cerebral vasculature while the vasculature is perfused with an oxygenated medium.

Methods according to the present invention comprise internally occluding blood flow to the arterial cerebral vasculature at a location(s) above the aortic arch. At a minimum, blood flow to the right cerebral vasculature will be internally occluded. Preferably, blood flow to both the right and left cerebral vasculature is internally occluded. Such internal occlusion is usually accomplished using an expansible occluder or partial occluder with central lumen, such as an inflatable balloon positioned at the distal end of a catheter, cannula, or other access device. The access device further provides for perfusion of an oxygenated medium into the occluded artery distal to the point of occlusion, e.g., the device may have a lumen that delivers the medium at a suitable positive pressure.

Occlusion of blood flow from the aortic arch and perfusion of oxygenated medium to the arterial cerebral vasculature may be accomplished in a number of ways, e.g., by occluding the right common carotid artery or by occluding an upstream portion of the brachiocephalic artery which-feeds the right carotid artery. In both cases, the oxygenated medium can be perfused distally of the balloon or other occluding device so that it flows up through the right common carotid artery into the cerebral vasculature. When occluding the brachiocephalic artery and perfusing the oxygenated medium upstream of the right common carotid artery, it may be desirable to at least partially inhibit blood flow through the right subdlavian artery, e.g. using another occluding balloon or using an externally applied tourniquet on the arm. Inhibiting the loss of oxygenated medium to the arm helps redirect the medium to the cerebral arterial vasculature through both the right common carotid artery as well as the right vertebral artery, assuming that the subdlavian artery is occluded at a point distal to the vertebral arterial branch. Other, more complex occlusion patterns could also be employed, although not necessarily being preferred.

Occlusion of blood flow from the aortic arch and perfusion of oxygenated medium to the left arterial cerebral vasculature may be effected within the left common carotid artery, the left subdlavian artery, and/or the left vertebral artery. When blood or other oxygenated medium is introduced into the left subdlavian artery, it may further be desirable to inhibit blood flow into the arm, e.g., by internally or externally occluding the left subdlavian artery at a point that prevents such blood flow.

In a presently preferred procedure, occluding balloons will be positioned within the brachiocephalic artery, the left common carotid artery, and the left subdlavian artery. Both the right subdlavian artery and the left subdlavian artery will be blocked, preferably with external tourniquets on the arms. Blood or other oxygenated medium will then be perfused into the arterial cerebral vasculature to points immediately upstream of each of the occluding balloons, preferably using lumens or other infusion components incorporated within the occluding devices themselves. Inhibition of blood flow down into the arms is beneficial since it redirects the blood or other oxygenated medium back into the cerebral arterial vasculature. While this approach may be optimal in many ways, the present invention can be carried out in other ways as well. Most simply, internal occlusion of the right brachiocephalic artery and perfusion of oxygenated medium distal to the point of occlusion may be sufficient in some cases by itself.

In many cases, it will be desirable to occlude the arteries at a point as close to the aortic arch as possible. In particular, this is true of the brachiocephalic artery, the left carotid artery, and the left subdlavian artery which branch directly from the aortic arch. Occlusion close to the aortic arch (i.e., immediately above the branch or within 3 cm thereof) is of benefit primarily because it enables the surgeon to access the artery and initiate the occlusion with minimal aortic dissection toward the neck. In other cases, of course, it will be possible to access any one of the brachiocephalic artery at a point close to the aortic arch and to intravascularly advance an occluding balloon or other devise to a desired point of occlusion. In some instances, it may even be desirable to deliver and position devices carrying multiple occluding balloons and/or lumens for delivering oxygenated medium to the cerebral arterial vasculature.

Access to the occlusion site and the target artery may be obtained in a variety of ways. For example, the target artery may be surgically exposed when the chest and neck are opened as part of a procedure being performed on the aortic arch. In such cases, small incisions can be made directly into the wall of the target artery to permit introduction of the occluder. Alternatively, in procedures that are performed away from the aortic arch and/or where it is not desired to surgically open the patient above the target sites within the arteries, the target sites can be accessed by conventional cut-down procedure or a needle-based procedure, such as the Seldinger technique. As yet another alternative, the arterial vasculature can be accessed at a LL point remote from the desired point of occlusion, e.g. in the femoral artery or in an artery of the arm, such as the axillary or brachial artery. The balloon or other occluding member on the catheter may then be intravascularly advanced from the access location to the desired point of occlusion in a conventional manner, e.g. over a guidewire under fluoroscopic observation. An approach to a desired occlusion point within the brachiocephalic artery and/or the right common carotid artery from an artery in the arm may be preferred since no catheter would be present in the aortic arch itself.

The oxygenated medium will usually be blood, more usually being autologous blood obtained from the patient being treated. In the most usual cases, patient blood will be recirculated through a conventional blood pump and oxygenator so that the patient may be continuously supplied with oxygen in the perfused cerebral vasculature. The blood or other oxygenated medium will also be cooled in order to induce selective hypothermia within the cerebral vasculature. A preferred hypothermic temperature for the brain will be in the range from 7° C. to 35° C., more preferably from 9° C. to 30° C. The actual temperature that is maintained will depend both on the temperature and the flow rate of the oxygenated medium, with higher flow rates generally requiring less cooling to achieve the target hypothermic temperature. Useful flow rates for the oxygenated medium will be in the range from 300 ml/minutes to 1500 ml/minutes, typically from 400 ml/minute to 1000 ml/minute without hypothermia, and from 80 ml/minute to 600 ml/minute, typically from 150 ml/minute to 400 ml/minute with hypothermia induced in the patient. Generally, the patient requires progressively less oxygen with increased hypothermia, allowing the flow rates of oxygenated cooled medium to be decreased. A sufficient flow of the oxygenated medium should be maintained, however, in order to maintain the desired level of hypothermia. Suitable temperatures will be in the range from 8° C. to 35° C., typically from 14° C. to 30° C. It will be appreciated, of course, that the values of temperature, flow rate, and degree of oxygenation will be quite interdependent in that particular optimum values might be selected for individual patients and/or for different procedures.

The methods of the present invention will-find their greatest use in open and thoracoscopic surgical procedures where the aorta is exposed and surgically opened to permit performance of the desired procedure. In such cases, the heart will be arrested and the perfusion of the oxygenated medium will be relied on to achieve adequate oxygenation of the brain tissue and to avoid deleterious ischemia. Generally, the flow rates and temperatures set forth above will be sufficient to both achieve adequate perfusion and avoid ischemia. After the open procedure is completed, and the aorta is surgically closed, heart function may be reestablished. In order to avoid the release of emboli from the aorta into the cerebral vasculature, occlusion of carotid artery(ies) will be maintained for a minimum amount of time after heart function has been reestablished, typically for at least about 2 minutes, preferably for at least about 5 minutes, in order to permit atheromatous debris and air to be cleared from the aorta and away from the brain.

Occlusion of the selected arteries with the expansible occluder may be achieved in a variety of ways. Usually, in open surgical procedures, the outside of the target artery(ies) will be surgically exposed, permitting surgical incisions through the arterial wall(s). The expansible occluder may then be introduced through the incision, expanded, and perfusion of oxygenated medium established through the occluder. Alternatively, the expandable occluders may be introduced percutaneously through the patient's neck and to the selected artery(ies) using conventional access techniques, such as the Seldinger technique. The expansible occluders will typically but not necessarily include catheters, cannulas, or other devices that permit the perfusion of the oxygenated medium through the expansible member and into the carotid artery for perfusion of the cerebral vasculature. It will also be possible to utilize separate devices for occlusion and for the perfusion of oxygenated medium. Fore example, it would be possible to employ an external clamp on the target artery and to utilize a separate needle or other cannula for infusion the oxygenated medium upstream of the clamp. The use of clamps, however, is generally not preferred since they can cause the release of significant amounts of atheromatous debris when released. It would also be possible to employ separate occluder(s) and infusion needles/cannulas, where the points of occlusion and infusion of oxygenated medium could be close together or spaced-apart. Also, as mentioned above, it will be possible to employ devices with more than one occlusion balloons and/or more than one infusion lumens in order to occlude and/or infuse oxygenated medium to different points in the vasculature from a single incision site.

As an alternative to access at points in the arterial vasculature above the aortic arch, the occlusion and perfusion devices may be introduced intravascularly through sites remote from the aortic arch. Most commonly, intravascular catheters may be introduced by conventional techniques through the femoral arteries and advanced to the target cerebral arteries using conventional techniques. Such access routes, will necessarily involve passing the catheters through the aortic arch itself. Thus, in many instances, it will be undesirable to use such intravascular techniques since they will lie within the regions where the procedure is being performed. Intravascular access could also be achieved in a retrograde manner through the axillary and brachial arteries as discussed above.

While it will be possible to perfuse a cold, oxygenated medium without collecting and recycling the medium, it will usually be desirable to establish a continuous extracorporeal flow circuit for filtering, oxygenating, and returning patient blood or other oxygenated medium to the patient. The oxygenated medium perfused into the arterial cerebral vasculature will generally flow through the anterior and posterior regions of the brain and into the venous system of the brain. From the venous system, the oxygenated medium will flow outwardly from the brain, primarily from the jugular veins. Thus, it will be convenient to collect the oxygenated medium from the brain from at least one of the right and left internal jugular veins, preferably from both internal jugular veins, or from the superior vena cava into which the jugular veins drain. This blood can then be returned to the extracorporeal blood pump, oxygenated, and cooled before return to the patient's arterial cerebral vasculature. Additionally, a very small portion of the blood or other oxygenated medium perfused into the brain through the cerebral arteries may leak back into the aortic arch through the left vertebral artery if the left subdlavian artery is not occluded. This leakage, typically in an amount from 5 ml/minute to 25 ml/minute, can be suctioned or otherwise collected by the surgeon and returned to the extracorporeal circulation system.

The brain and cerebral vasculature are at greatest risk from embolization and ischemia during the performance of aortic procedures that require arresting of the heart. Other portions and tissues within the body, however, are also at significant risk and in some cases it may be desirable to establish a perfusion of oxygenated medium through the noncerebral vasculature, in particular the vasculature in the lower portion of the patient's body. For example, oxygenated blood or other medium can be introduced into the aorta below the aortic arch, where the aortic arch is isolated using an expansible occluder or other conventional occlusion device. The oxygenated medium will thus flow to the lower portion of the patient's body where it will collect in the venous system and be returned towards the patient's heart through the inferior vena cava. By occluding the inferior vena cava, again typically using an expansible occluder, the blood or other oxygenated medium may be collected and returned to an extracorporeal oxygenation, pumping, and optional cooling circuit.

The present invention still further provides kits including one or more expansible occluders adapted to occlude selected artery(ies) as described above. Such kits will further include instructions for use according to any of the methods set forth above. Additionally, the kit may comprise a package for holding all or a portion of the kit components, typically in a sterile condition. Typical packages include trays, pouches, boxes, tubes, and the like. Preferably, the cannulas will each have an occlusion balloon sized to occlude the respective blood vessel lumen into which they are placed. Other optional kit components include oxygenated medium, drugs to be delivered via the flowing blood or other oxygenated medium, catheters for connecting the cannulas to an extracorporeal recirculation/oxygenation cooling system, cassettes for use with such extracorporeal recirculation systems, cooling elements, thermometers, pressure transducers, and the like.

BRIEF DESCRIPTION OF THE DRAWINGS

FIGS. 2A and 2B illustrate the use of a pair of access cannulas for perfusing oxygenated medium through the cerebral vasculature of a patient according to the methods of the present invention.

DESCRIPTION OF THE SPECIFIC EMBODIMENTS

Figure 1:
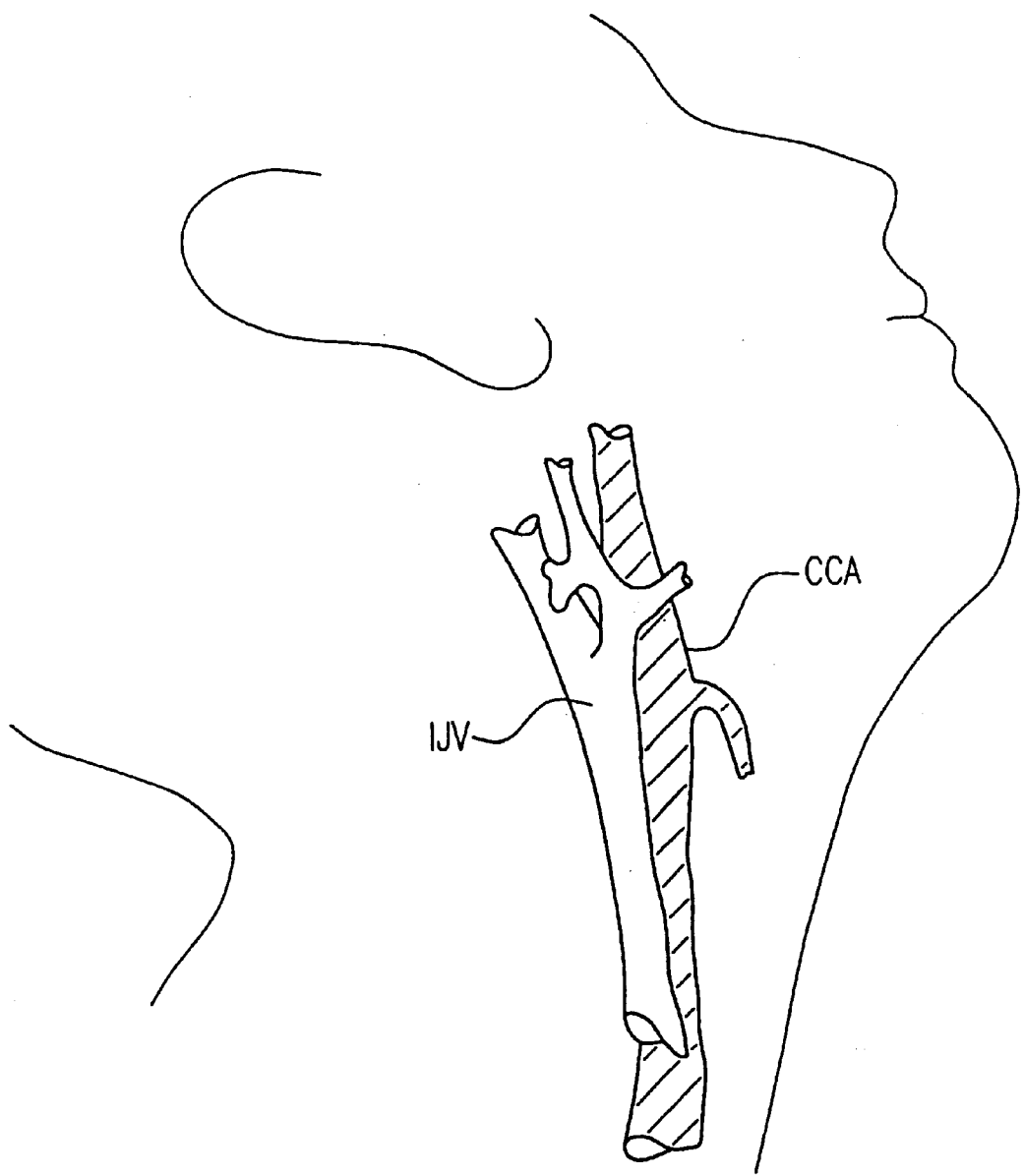
FIG. 1 is a schematic illustration of a patient's head illustrating arterial and venous access sites suitable for use in the methods of the present invention.

The present invention provides methods, systems, and kits for perfusing the cerebral vasculature of a patient with an oxygenated medium. For the purposes of the present invention, the cerebral vasculature includes all arteries and veins leading into or from the patient's head, particularly including the common carotid arteries, the external and internal carotid arteries, and all smaller arteries which branch from the main arteries leading into the head. In some cases, particularly in open surgical procedures, access may be established in the aortic arch and innominate (brachycephalic trunk) artery as well. Cerebral veins include the external and internal jugular veins, the superior vena cava, and the smaller veins which feed into the primary veins draining the cerebral vasculature. Preferred access points should be at locations in the vasculature which permit relatively direct percutaneous introduction of a needle, cannula, or other access conduit through which the flow of oxygenated medium will be established. Exemplary access sites are in those regions of the internal jugular vein IJV and common carotid artery CCA which are readily located and accessed through a patient's neck, as illustrated in FIG. 1.

Usually, only a single arterial and a single venous site need be accessed. Blood or other oxygenated medium perfused at a flow rate of at least 0.2 l/min (preferably at least 0.5 l/min) will usually be sufficient to go up from the arterial access site, e.g., through either the right or left common carotid artery, perfuse the ipsilateral hemisphere, and to cross over and perfuse the An contralateral hemisphere of the brain. Suitable perfusion pressures are in the range from 250 mmHg, preferably from 30 mmHg to 160 mmHg. The ipsilateral hemisphere will thus be perfused in an antegrade direction while the contralateral hemisphere and territories supplied by the posterior circulation will be perfused in a retrograde direction. The blood will then flow into the cerebral venous vasculature from where it may be collected at one or two venous access sites. In this way, the entire brain can be perfused with oxygenated and optionally cooled blood or other oxygenated medium.

As illustrated in FIGS. 2A and 2B, access will usually be established using cannulas 10 and 20, each having inflatable isolation balloons 12 and 22 near their distal ends, respectively. In the illustrated embodiment, the cannulas 10 and 20 are needles having sharpened distal tips such that the needles may be penetrated through the patient's skin S without the need to employ separate stylets, needles, or other access means. The treating personnel are thus able to locate the appropriate access points on the patient's neck or other location and directly introduce the cannulas 10 and 20 so that their distal tips lie within the lumens of the artery A and vein V, respectively. Alternatively, the treating professional may access the artery and/or vein through a small incision or puncture allowing introduction of a blunt cannula or other access tube.

Once the cannulas 10 and 20 have been placed, as illustrated in FIG. 2A, the balloons 12 and 22 will be inflated, as illustrated in FIG. 2B. The balloons and 12 and 22 partition the cerebral vasculature so that oxygenated medium introduced through the arterial cannula 10 will travel upwardly into the cerebral vasculature and will be inhibited from flowing downwardly to the arterial system below the head. Similarly, the balloon 22 on the venous cannula 20 will prevent the outflow of blood or other oxygenated medium from the cerebral vasculature from flowing downwardly from the head, allowing efficient collection of the outflow by the cannula 20.

In the simplest cases, the methods of the present invention may rely on providing relatively large volumes of oxygenated medium, such as a pre-oxygenated carrier, such as a perfluorocarbon, or pre-oxygenated heterologous blood, and flowing the oxygenated medium through the arterial cannula 10, through the cerebral vasculature, and out the venous cannula 20 in a once-through manner. The oxygenated medium passing out of the venous cannula will not be recirculated.

Figure 3:
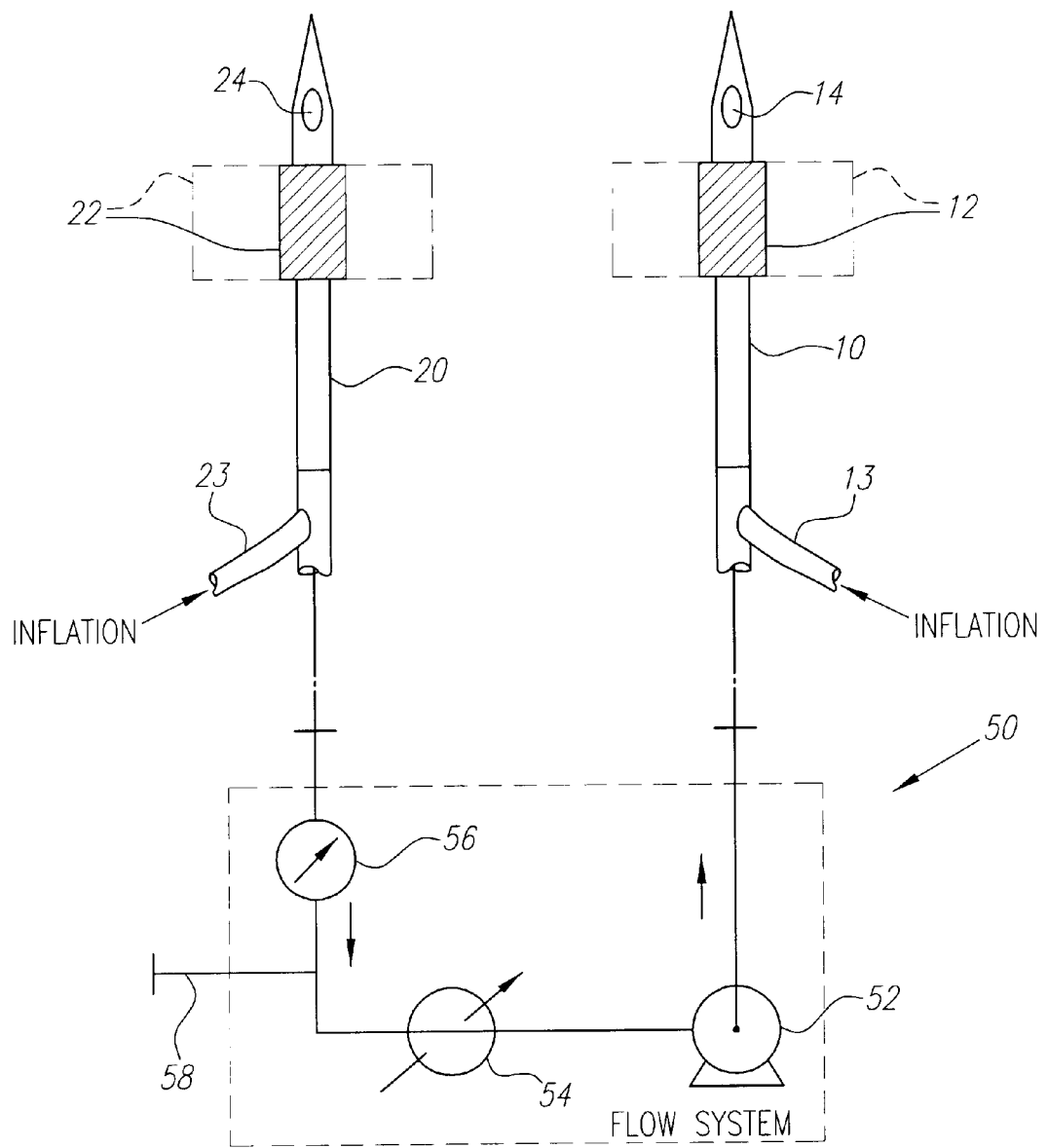
FIG. 3 illustrates a preferred system constructed in accordance with the principles of the present invention.

More typically, however, the methods of the present invention will rely on circulating the oxygenated medium from the venous cannula 20 back to the arterial cannula 10. To circulate the oxygenated medium, it will usually be necessary to oxygenate the medium externally of the patient, further usually being desirable to also cool the medium to lower the temperature of the brain. Such external oxygenation and optional cooling may be provided by a system 50 as illustrated in FIG. 3. The system 50 includes a pump 52, typically a peristaltic pump, a cooler 54, a temperature gauge 56, and a port 58 for infusing cerebral protective agents and/or other drugs or biologically active substances. Such systems are analogous to the cardiopulmonary bypass systems used in heart and vascular surgery. Suitable portable bypass pumps and oxygenators are described in U.S. Pat. No. 4,540,399; U.S. Pat. No. 5,011,469; and U.S. Pat. No. 5,149,321, the full disclosures of which are incorporated herein by reference. The systems described in these patents, however, are generally intended for maintaining artificial circulation through all or a substantial portion of the patient's entire vasculature. The systems of the present invention will generally be modified to provide blood or other oxygenated medium at lower flow rates within the ranges set forth above.

Optional features of the cannulas 10 and 20 illustrated in FIG. 3 include separate inflation conduits 13 and 23 for inflating balloons 12 and 22, respectively. The inflation conduits may be connected to syringes or other conventional devices for selectively inflating the balloons after the cannulas 10 and 12 have been properly positioned within the target blood vessels. Additionally, ports 14 and 24 may be provided near the sharpened distal tips of the cannulas 10 and 12, respectively. Alternatively, the distal tips of the cannulas could simply have a chamfered, sharpened distal tip where flow passes directly out the tip. As a further alternative, the cannulas 10 and 12 could be provided with simple stylets which permit self-introduction. After introduction, the stylets could be quickly removed to provide an open flow lumen at the tip.

Figure 4:
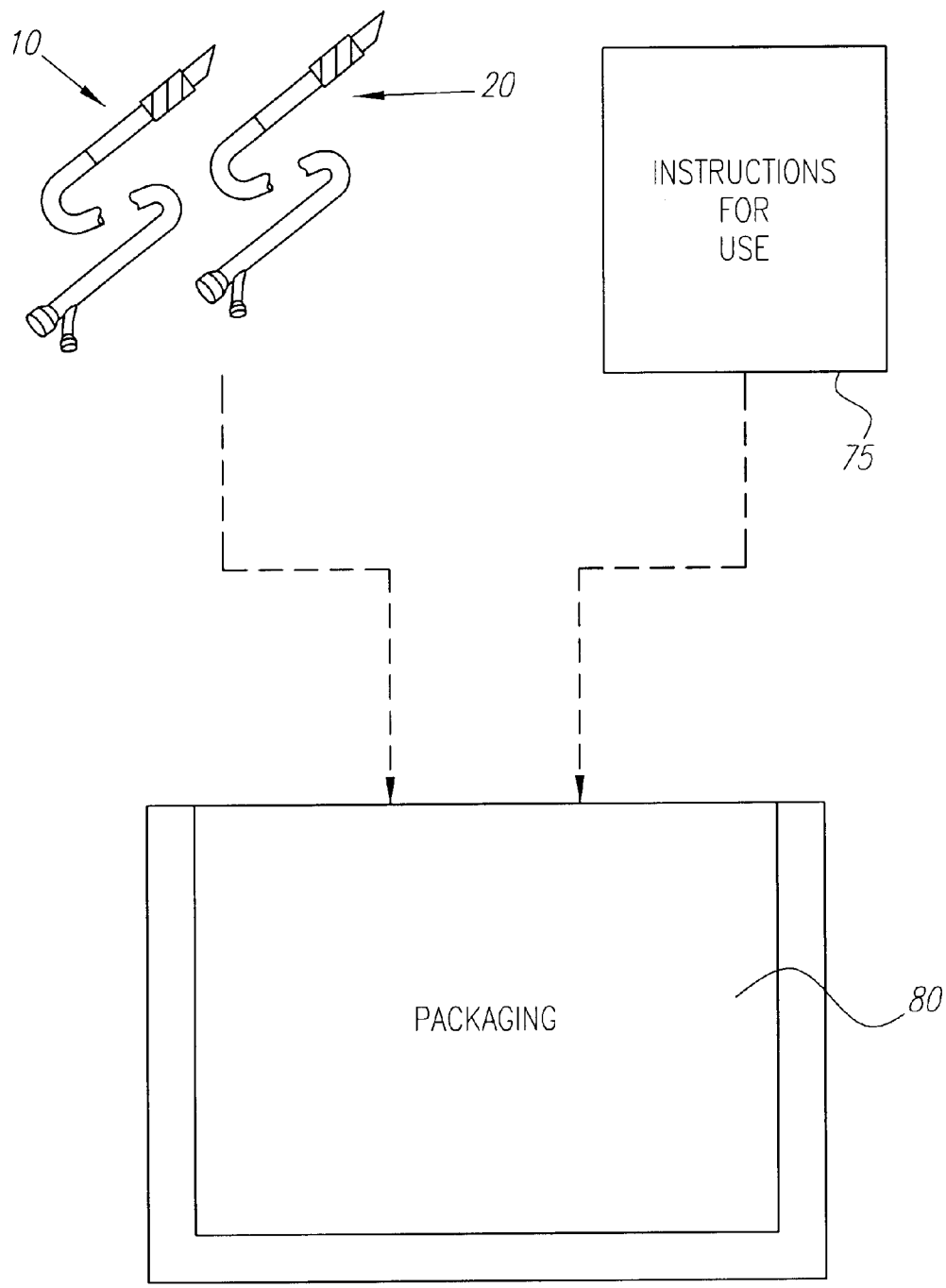
FIG. 4 illustrates an exemplary kit constructed in accordance with the principles of the present invention.

Referring now to FIG. 4, kits according to the present invention will comprise at least cannulas 10 and 20 and instructions for use (IFU) 75. The cannulas 10 and 20 will be suitable for connection to an extracorporeal flow system 50, or for connection to a reservoir of oxygenated medium, depending on the intended use. The instructions for use 75 will set forth any of the methods described above. Usually, the catheters 10 and 20 and instructions for use 75 will be packaged together in a suitable package 80, such as a pouch, tray, box, tube, or the like. Optionally, the instructions for use may be printed in whole or in part on a portion of the packaging 80. Usually, at least the catheters 10 and 20 will be sterilely maintained within the package 80. Other optional kit components which could be placed within the package 80 include oxygenated medium, cerebral protective agents and/or other drugs, additional catheters for connecting the cannulas to system 50 or other extracorporeal apparatus, replaceable cassettes for system 50 which permit replacement of all system components which directly contact the blood, and the like.

Figure 5:
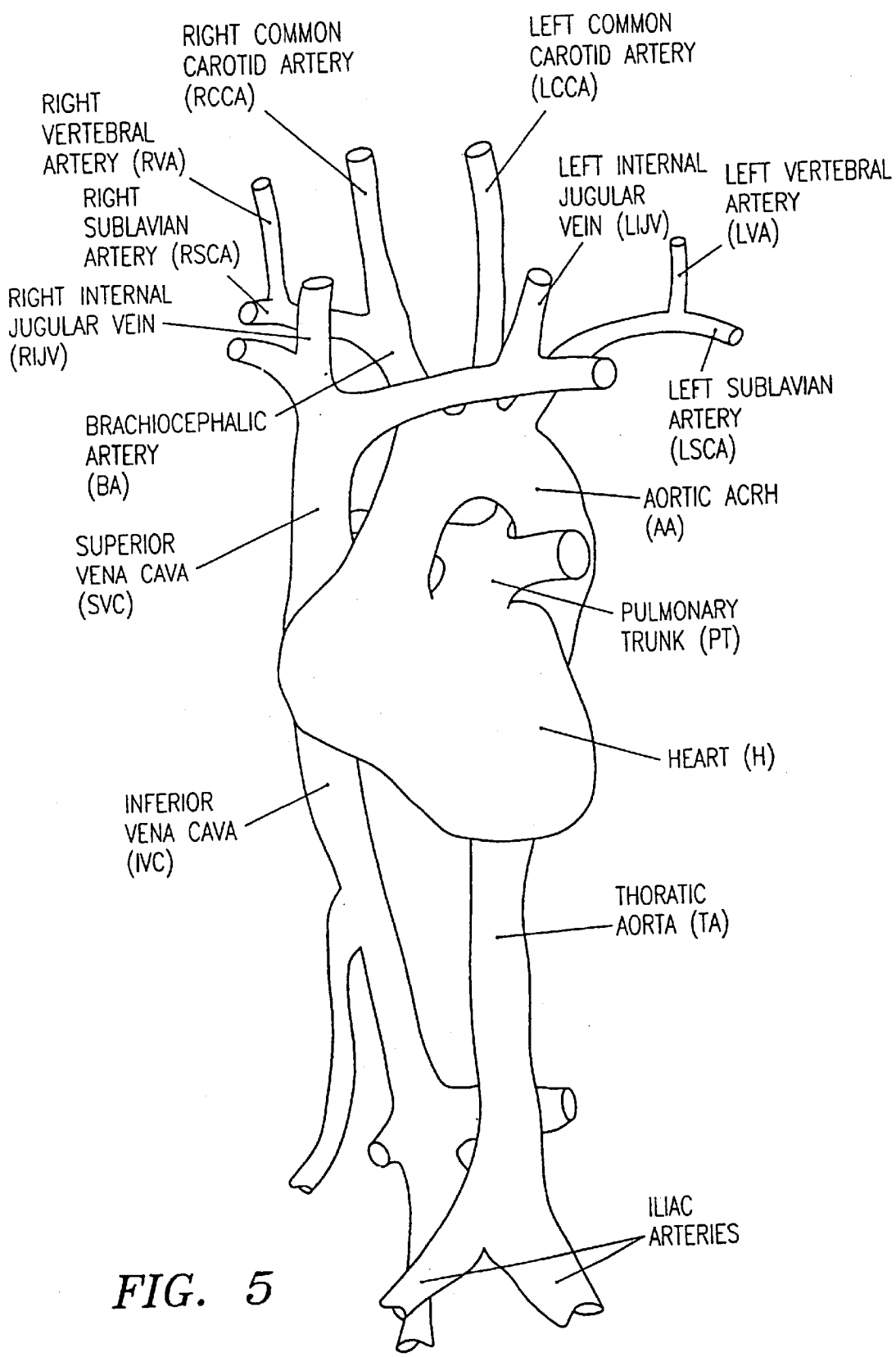
FIG. 5 illustrates the great vessels that exit and enter the heart and which are relevant to the occlusion and circulation patterns of the present invention.

Referring now to FIG. 5, systemic circulation relevant to the methods of the present invention will be briefly described. Oxygenated blood from the heart normally flows upwardly through the aortic arch and then downward to the lower portions of the body through the thoracic aorta. Three major arteries extend upwardly from the top of the aortic arch. The brachiocephalic artery branches into the right carotid artery and the right subdlavian artery. In contrast, the left carotid artery and left subdlavian artery extend directly from the aortic arch and do not have a common portion. Together, the right common carotid artery and left common carotid artery provide oxygenated blood to most parts of the head and neck. They ascend through the anterior neck just lateral to the trachea and are covered by relatively thin muscles which permits direct percutaneous access via cutdown or needle introduction (the Seldinger technique) in certain embodiments of the present invention. In addition to the carotid arteries, oxygenated blood is provided to the brain through the vertebral arteries, although to a significantly lesser extent.

As will be described in more detail below, the methods of the present invention will rely on internally occluding blood flow from the aortic arch to at least one common carotid artery, and preferably both common carotid arteries. Occlusion of blood flow from the aortic arch to the right common carotid artery may be effected by occluding the blood flow lumen in the brachiocephalic artery and/or the right common carotid artery itself. Occlusion of the left common carotid artery will take place in a lumen of the left common carotid artery itself, and optionally either or both of the right and left vertebral arteries may also be directly or indirectly occluded. Blood or other oxygenated medium will be provided to the cerebral arterial vasculature through at least some of the occluded arteries by perfusing a medium to the artery(ies) at a point distal to the occlusion. As the carotid arteries supply most of the blood flow to the brain, it will not be necessary to occlude the vertebral arteries and/or provide oxygenated blood to the brain through the vertebral arteries. While some leakage of blood back to the aorta may occur through the vertebral arteries, such leakage is minor and can be removed from the aortic arch using conventional suction devices.

By occluding blood flow to the right common carotid artery using an occluder present in the brachiocephalic artery, blood supplied distal to the occluder will flow to both the right common carotid artery and the right vertebral artery. Thus, it will usually be preferred to occlude flow to the right common carotid artery at a point within the brachiocephalic artery. It will be appreciated, of course, that by providing the perfusion of oxygenated medium distally of the brachiocephalic artery, blood will flow not only to the right common carotid artery and right vertebral artery, but also toward the arm through the right subclavian artery. Thus, in order to inhibit the flow of oxygenated medium to the arm and redirect such flow to the cerebral arteries, it will in some cases be desirable to provide a tourniquet on the right arm. Alternatively, an occlusion balloon could be located within the lumen of the right subclavian artery to point downstream from the right vertebral artery branch. Optionally, a catheter having a pair of balloons could be used, where one balloon occludes within the brachiocephalic artery and a second, more distal balloon occludes within the right subclavian artery.

Occlusion of the left vertebral artery may be effected in either the left subclavian artery, usually at a point near the branch with the aortic arch, or within the left vertebral artery itself. Occlusion within the left subclavian artery is generally preferred since it will inhibit passage of atheromatous material into the entire arterial structure branching from the left subclavian artery. Moreover, by perfusing oxygenated medium beyond the point of occlusion, that medium will flow into the left vertebral artery to supply the left cerebral arterial vasculature. Loss of blood to the patient's arm can be inhibited by applying a tourniquet to the left arm.

The venous system of the brain drains primarily through the right internal jugular vein and the left-internal jugular vein. These veins, in turn, drain into the superior vena cave where the oxygen-depleted blood is returned to the heart. Blood supplied to the lower body through the thoracic aorta returns to the heart through the inferior vena cava.

Figure 6A:
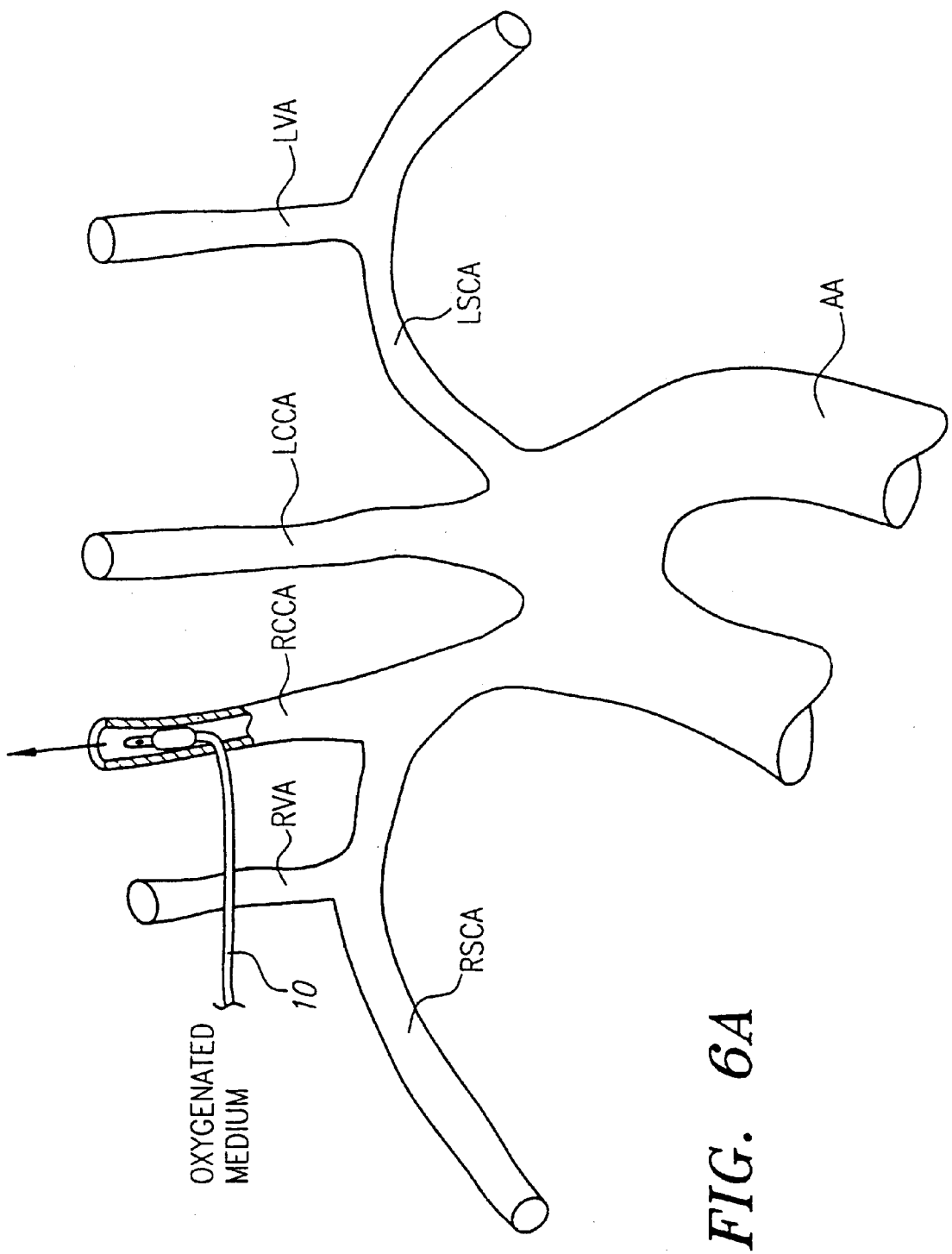
FIGS. 6A–6E illustrate the use of differing arrangements of expansible occluders for occluding and directing the flow of oxygenated medium to the cerebral arteries according to the methods of the present invention.

Referring now to FIG. 6A, a first exemplary method for accessing an aorta according to the present invention comprises internally occluding the right common carotid artery at a point above the aortic arch. Typically, the occlusion may be achieved using expansible occluders, such as balloon-tipped cannula 10 that is placed in a lumen of the right common carotid artery. The balloon may be any conventional type of balloon commonly used for blood lumen occlusion, e.g., being elastomeric balloons having a generally spherical geometry. The balloons will be expandable to a size in the range from 3 mm to 20 mm, typically at a relatively low inflation pressure on the order of 2 atmospheres to 5 atmospheres. The expansible occluders may be introduced surgically, percutaneously, or intravascularly, as discussed above.

Most commonly, the surgeon accessing the aorta will extend the incision so that the exterior surfaces of each carotid artery are exposed. A small surgical incision can then be made and the exposed wall of the artery and the occlusion balloon introduced in a conventional manner. Alternatively, the balloon may be percutaneously introduced via a cut-down procedure or using a needle, guidewire, and appropriate insertion sheath using conventional techniques, such as the Seldinger technique. In all cases, after occlusion is achieved, the oxygenated medium may be introduced through the cannula, typically within the flow rate and temperature ranges set forth above. It will also be desirable to monitor and control the pressure of the oxygenated medium being introduced, typically within a range of about 10 mmHg to 200 mmHg, preferably from 30 mmHg to 90 mmHg. The blood may be introduced in a continuous, non-pulsatile flow.

Figure 6B:
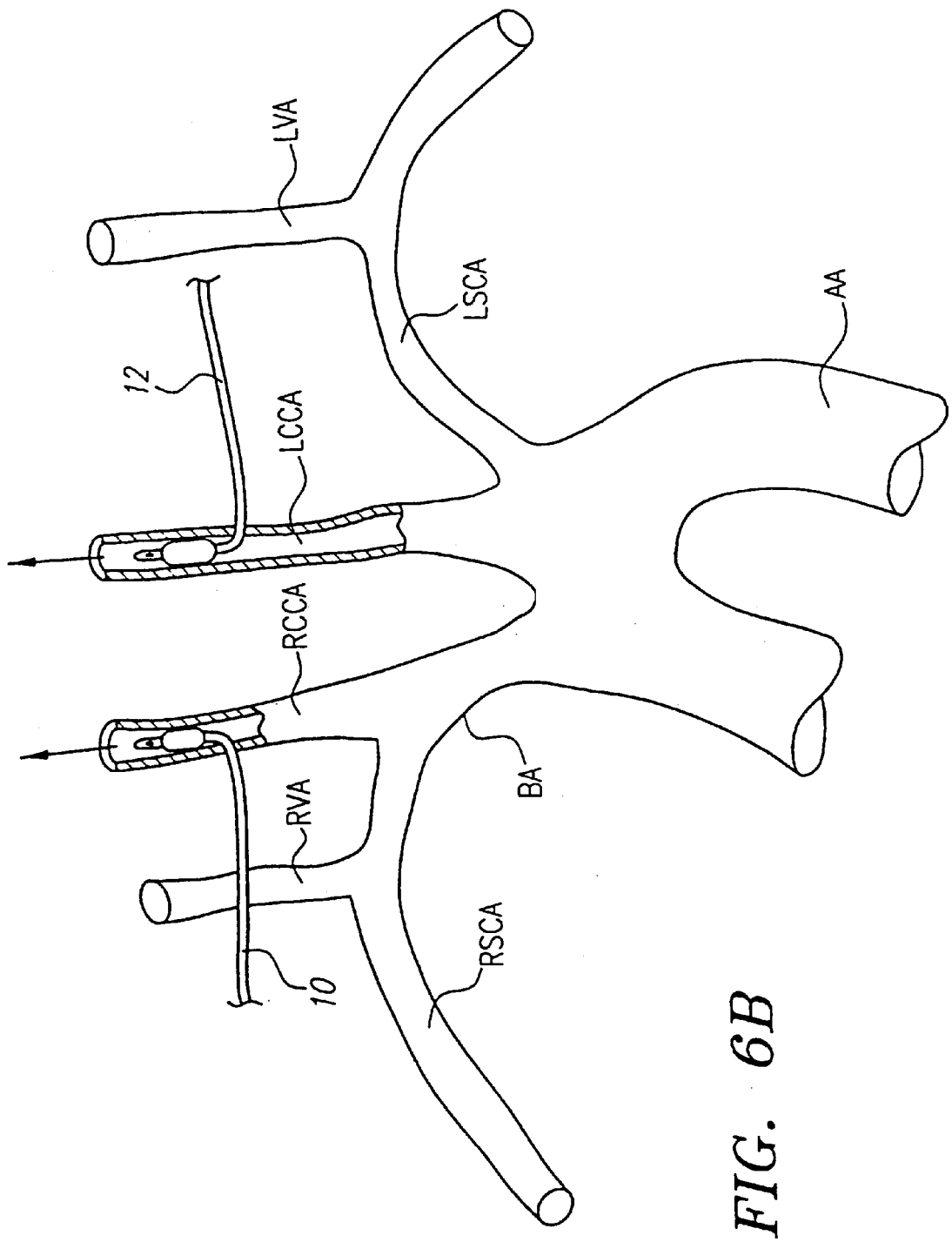
Figure 6C:
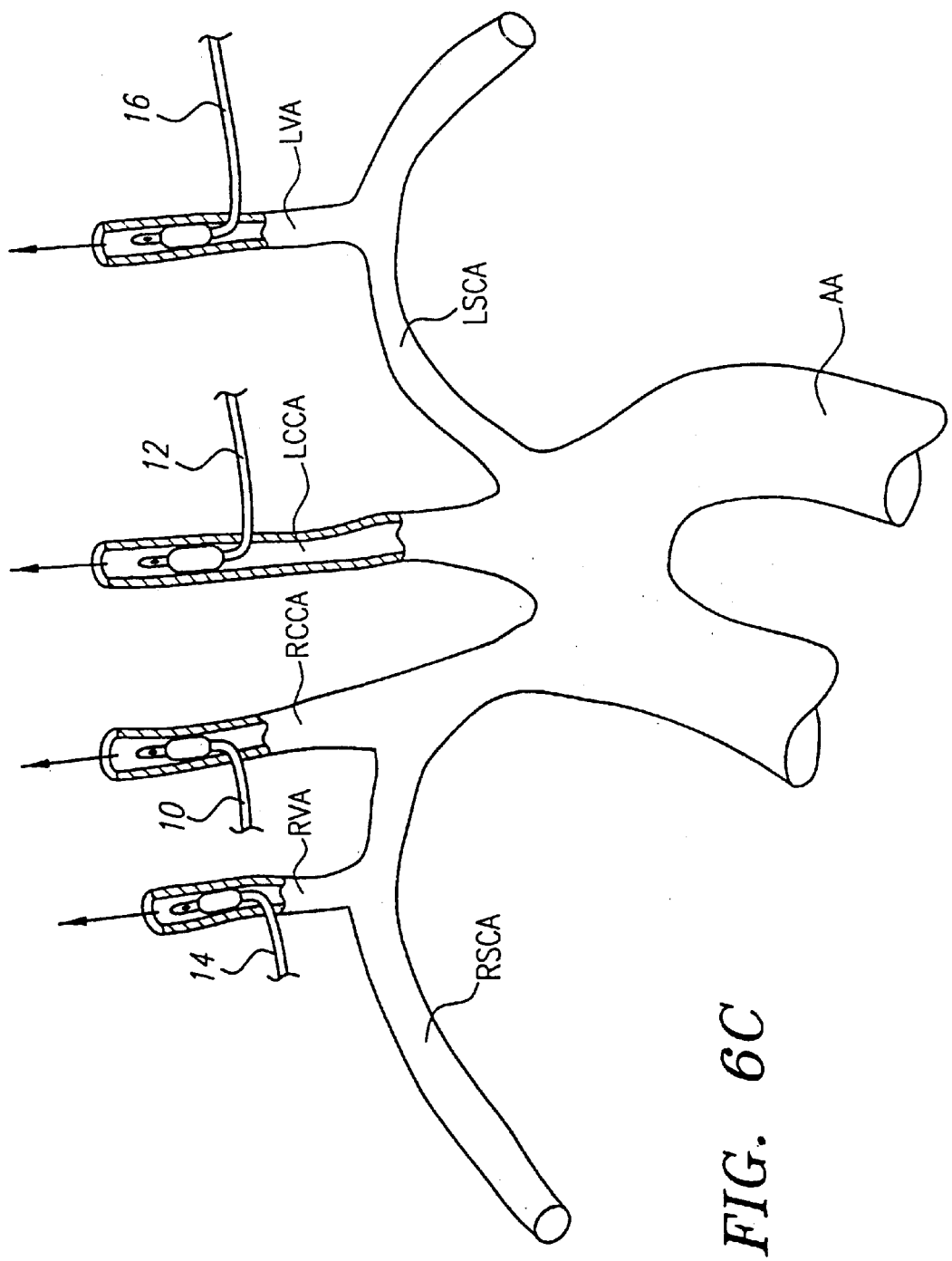

By occluding only the right common carotid artery, as shown in FIG. 6A, the oxygenated medium will be provided only to the right arterial cerebral vasculature. Moreover, as none of the right vertebral artery, left common carotid artery, nor left vertebral artery are occluded, those arteries are placed at risk at receiving atheromatous material, particularly when heart function is reestablished. Thus, it will frequently be desirable to occlude at least the right common carotid artery with the balloon-tipped cannula 10 and the left common carotid artery with a second balloon-tipped cannula 12, as shown in FIG. 6B. Oxygenated medium may then be perfused through either or both of the cannulas 10 and 12, preferably through both. Further optionally, cannulas 10, 12, 14, and 16 may be disposed within the lumens of the right common carotid artery, left common carotid artery, right vertebral artery, and left vertebral artery, respectively, as shown in FIG. 6C. Such an arrangement is advantageous because it both reduces the risk of entry of atheromatous material into the cerebral vasculature and provides for multiple access points for introducing oxygenated medium to the cerebral vasculature.

Figure 6D:
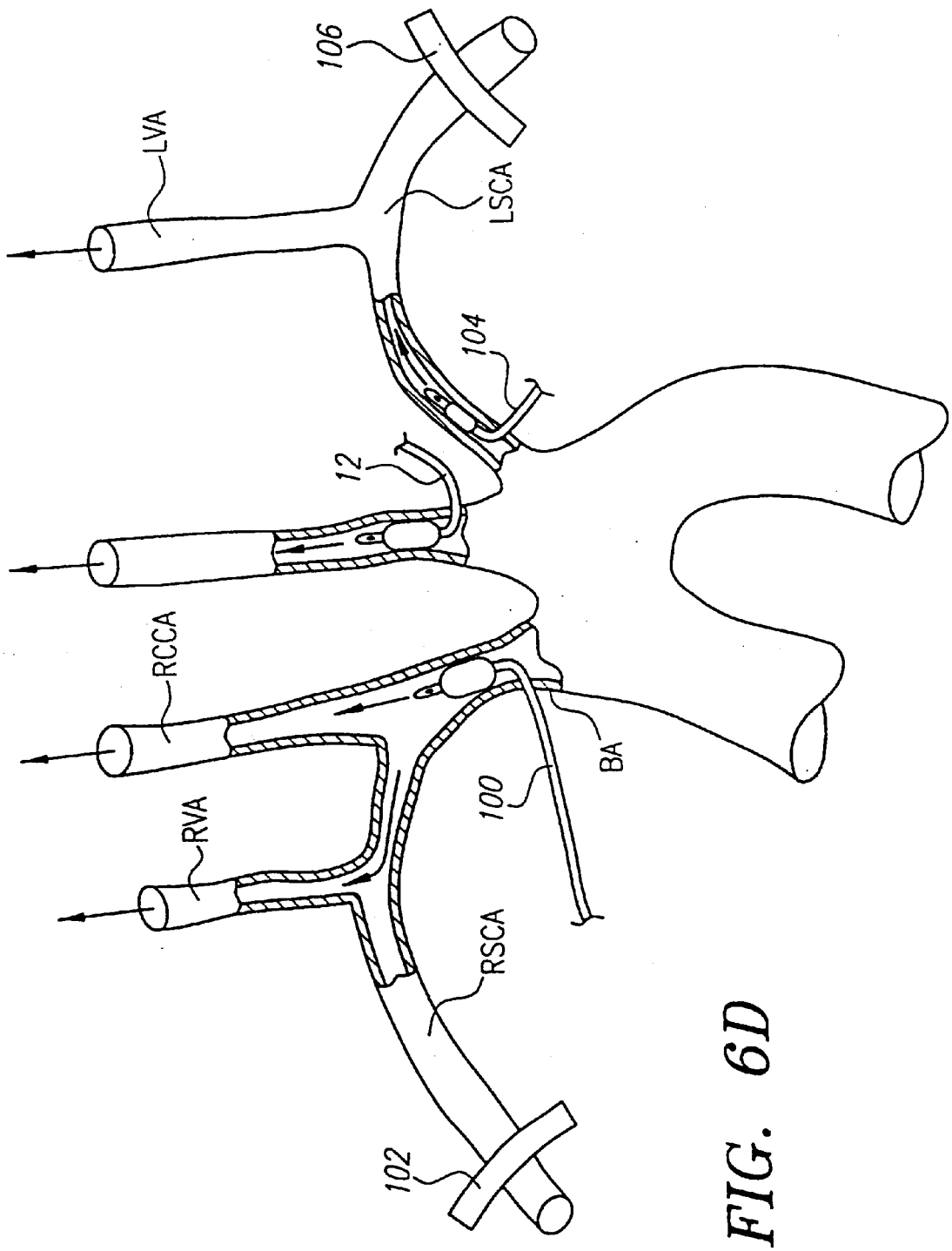

The arrangement of cannulas shown in FIG. 6C is not optimal for at least two reasons. First, it requires the use of four separate cannulas. Second, atheromatous material from the aortic arch can enter both the right subclavian artery and the left subelavian artery since the entry points to these arteries are not occluded. Thus, an improved arrangement of multiple cannulas is shown in FIG. 6D. There, a first balloon-tipped cannula 100 is placed into the brachiocephalic artery and positioned to perfuse oxygenated medium to the cerebral vasculature through both the right common carotid artery and right vertebral artery. Loss of oxygenated medium to the right arm may be inhibited by placing a tourniquet 102 on the arm. A second balloon-tipped catheter 12 may be placed in the left common carotid artery, generally as described above. A third balloon-tipped catheter 104 is placed in the left subclavian artery relatively near the branch point from the aortic arch. Placement near the aortic arch branch will enhance the isolation of the arterial system branching from the left subclavian artery. Moreover, oxygenated medium perfused distally of the balloon-tipped cannula 104 will flow upwardly through the left vertebral artery into the left cerebral arterial vasculature. Loss of such oxygenated medium may be inhibited by placing a second tourniquet 106 on the patient's left arm.

Figure 6E:
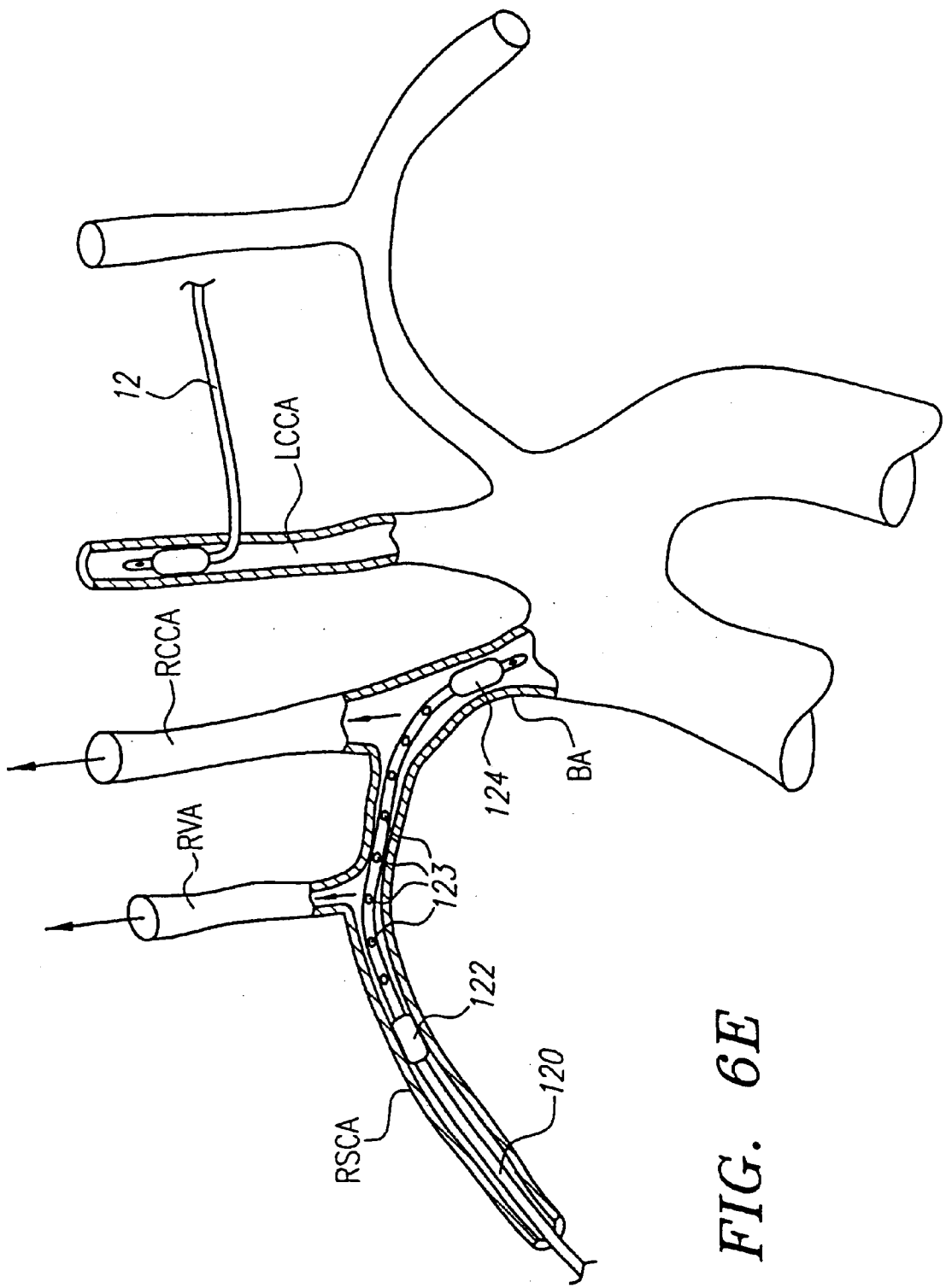

As illustrated thus far, the balloon-tipped cannulas have included only single balloons and have been introduced through the vascular wall at a point immediately adjacent to the point of occlusion. As discussed above, however, the cannulas need not be introduced adjacent to the point of occlusion nor do they need to be simple, single-balloon catheters. An alternative balloon-tipped catheter arrangement employing a cannula 120 having a pair of a balloons 122 and 124 as illustrated in FIG. 6E. The cannula 120 may be introduced in a retrograde fashion through the right subclavian artery, optionally from an artery of the arm, such as the axillary artery or the brachial artery. The cannula 120 is advanced so that the distal-most balloon 124 is disposed within the lumen of the brachiocephalic artery. By inflating the balloon 124, blood flow from the aortic arch to the vasculature above the brachiocephalic artery is occluded. By inflating balloon 122, blood flow through the right subclavian artery at points distal to the branch of the right vertebral artery is also occluded. Perfusion ports 123 are provided on the cannula 120 between the distal-most balloon 124 and second balloon 122, and oxygenated medium may be introduced through the perfusion ports to flow to both the right vertebral artery and the right common carotid artery. Moreover, flow out the right subclavian artery beyond balloon 122 is also occluded, helping to direct substantially all flow of oxygenated medium to the cerebral vasculature. Usually, the second balloon-tipped catheter 12 will be disposed within the left common carotid artery and further optionally (although not shown) one or more balloon-tipped catheters may be used to occlude flow to the left vertebral artery, as shown in either FIGS. 6C or 6D.

Figure 7:
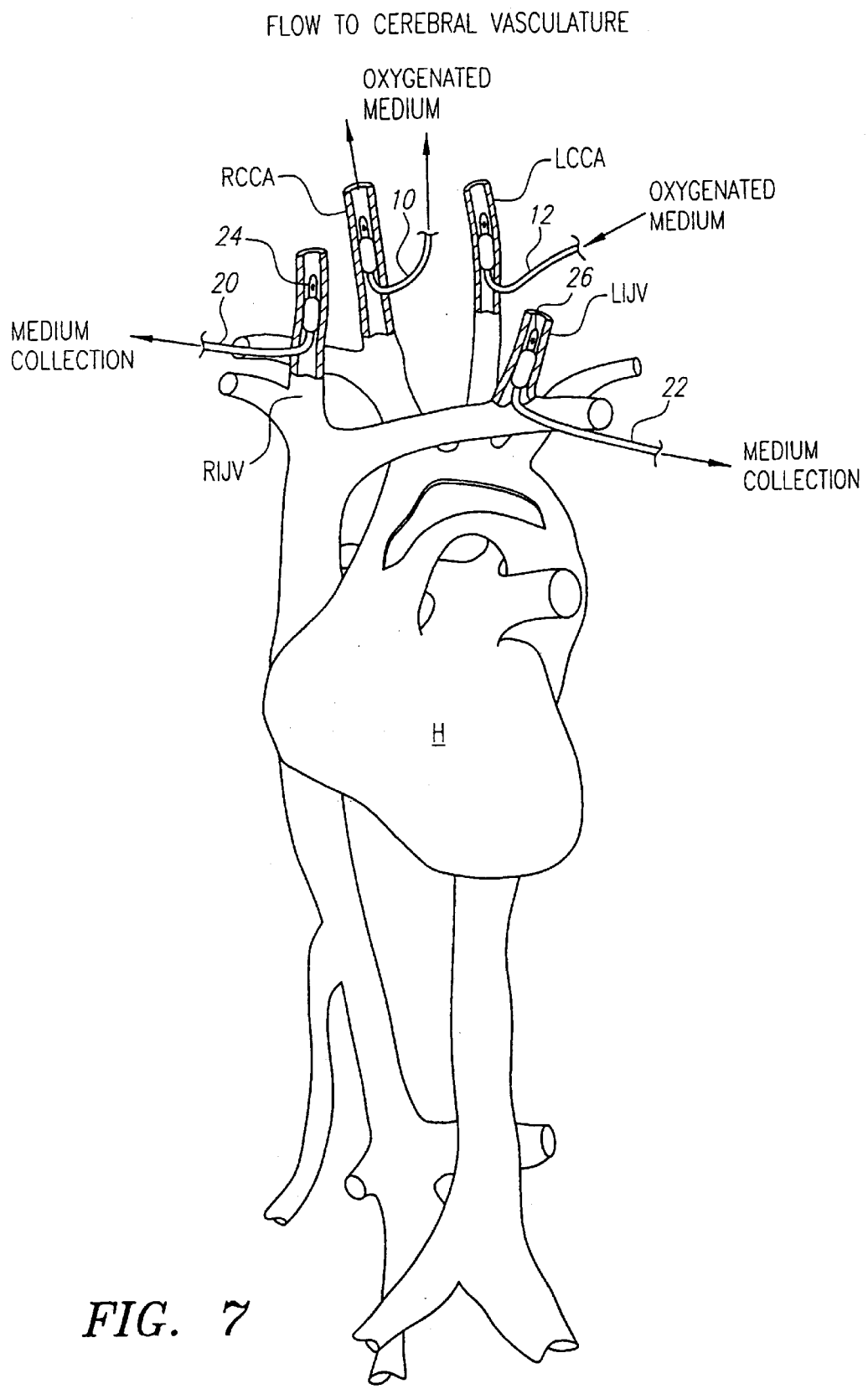
FIG. 7 illustrates the occlusion pattern of FIG. 6, with further occlusion of the internal jugular veins to collect oxygenated medium flowing from the venous structure of the brain.
Figure 8:
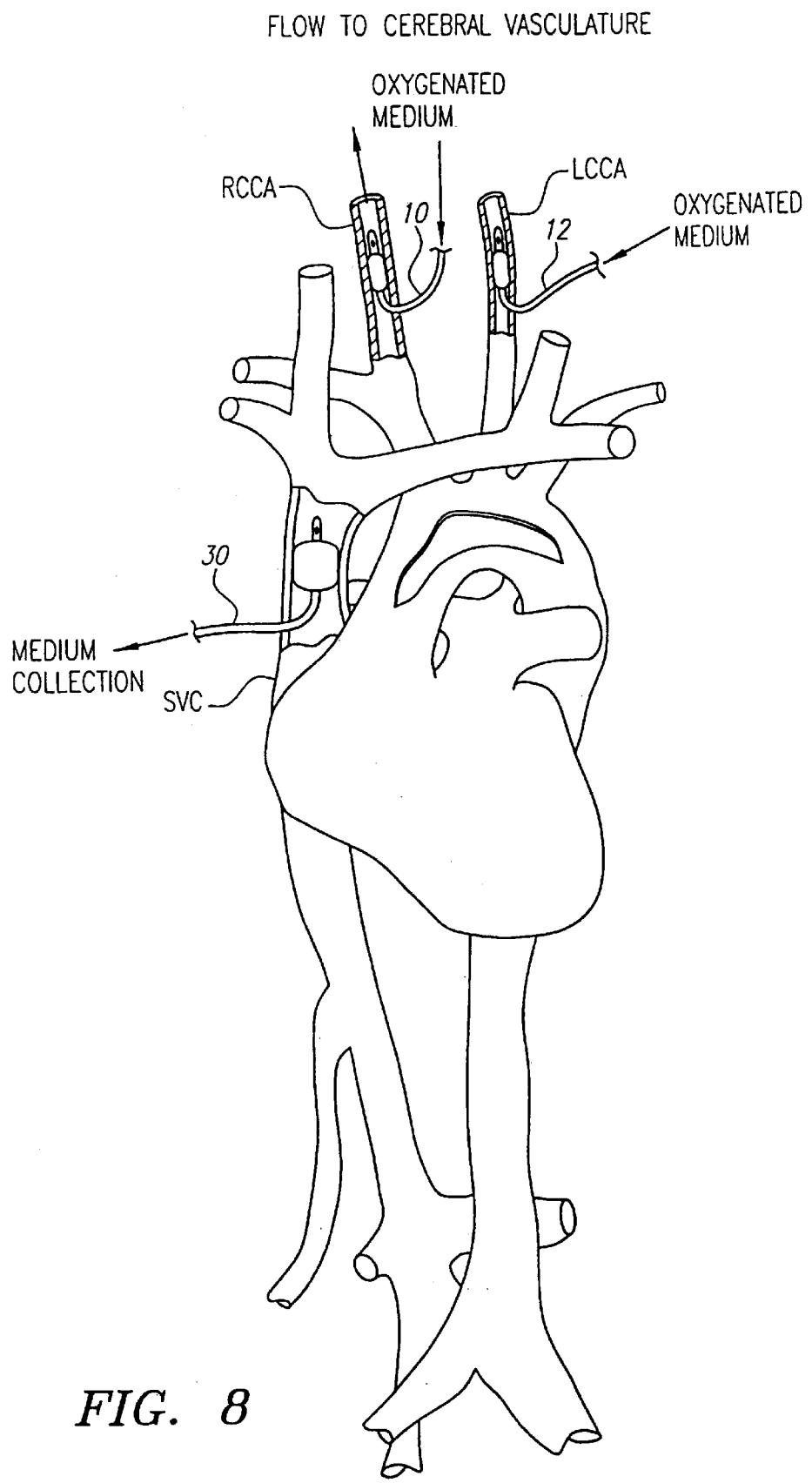
FIG. 8 illustrates an alternate occlusion pattern for collecting oxygenated medium from the brain, where the superior vena cava is occluded and all medium flowing into the superior vena cava collected.

When the oxygenated medium is autologous patient blood, it will be necessary to collect at least a portion of the oxygen-depleted blood after it has passed through the cerebral vasculature and to return that blood to the patient after filtering, reoxygenation, and optional cooling. The blood may be collected in the venous vasculature which drains the brain, typically by placing a pair of expansible occluders 20 and 22 into the right internal jugular vein and left internal jugular vein, respectively, as illustrated in FIG. 7. The expansible occluder 20 and 22 may be constructed similarly to the expansible occluders 10 and 12, but will include distal tips 24 and 26, respectively, having a plurality of ports adapted to collect the oxygen depleted blood as it flows toward the heart. As an alternative to blocking the internal jugular veins with a pair of expansible occluders, the superior vena cava may be blocked with a single expansible occluder 30, as illustrated in FIG. 8. In both cases, the blood or other oxygen depleted medium collected in the venous side of the vasculature will be returned to an extracorporeal system for reoxygenation, pumping, and optional cooling, as will be described in more detail in connection with FIG. 10 below. The expansible occluders 20, 22, and 30, will be sized and adapted to be surgically or percutaneously introduced to the associated vein.

Figure 9:
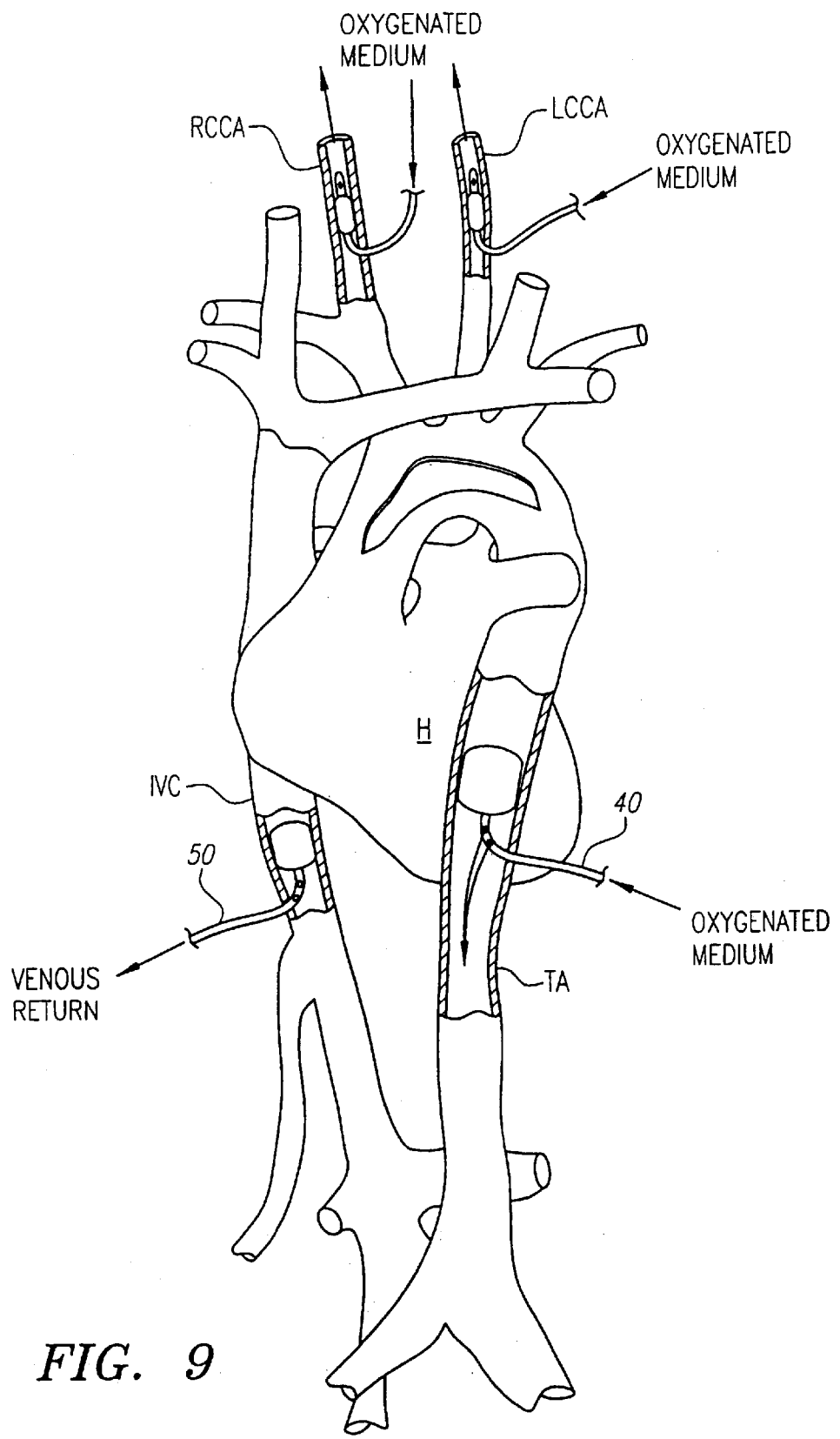
FIG. 9 illustrates an occlusion pattern according to the present invention where the lower vasculature of the patient is occluded and perfused with oxygenated medium.

In addition to isolation and perfusion of the cerebral vasculature by any of the techniques described above, the present invention also provides for optional perfusion of non-cerebral portions of the patient vasculature, particularly the lower body vasculature as illustrated in FIG. 9. Conveniently, the lower body vasculature may be perfused by introducing blood or other oxygenated medium into the descending aorta using an expansible occluder 40, typically a balloon catheter, optionally a balloon catheter adapted for introduction through the femoral artery in a conventional manner. The expansible occluder 40 will include flow ports, which are disposed below the balloon when a catheter is placed within the thoracic aorta. This way, the oxygenated medium will flow downwardly from the balloon into the lower arterial vasculature. After perfusing through tissue in the lower body, the oxygen depleted blood or other medium will flow into the venous system and ultimately upwardly through the inferior vena cava. By placing an expansible occluder 50 within the lumen of the inferior vena cava may be occluded and the return blood flow collected. The collected blood may then be circulated through an extracorporeal recirculation system, as described in more detail in connection with FIG. 10.

Figure 10:
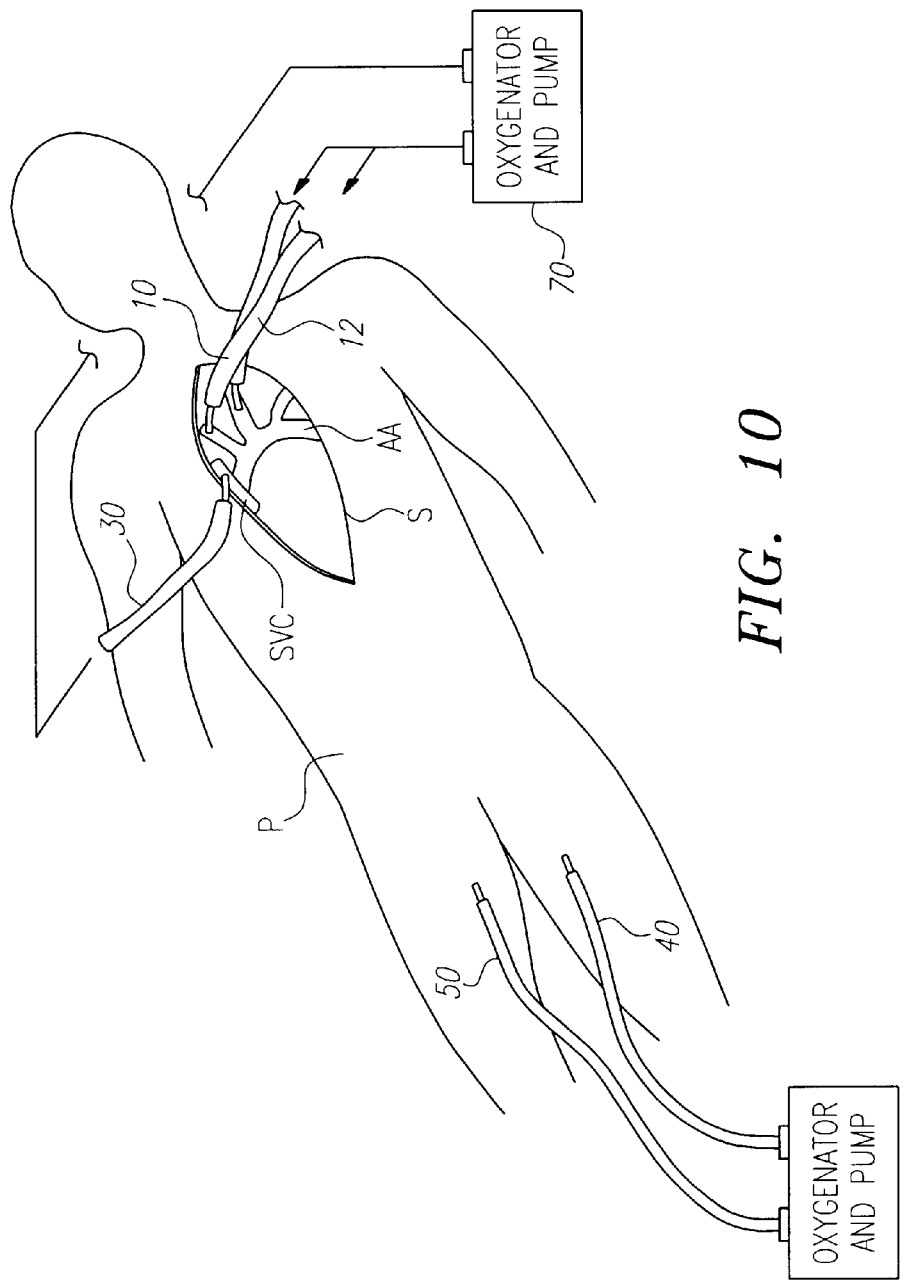
FIG. 10 is a schematic illustration of a patient undergoing an aortic procedure with an oxygenated medium being supplied according to the scheme set forth in FIGS. 8 and 9.

Referring now to FIG. 10, a patient P is undergoing an open surgical procedure through a sternotomy S that exposes the aortic arch AA and the superior vena cava SVC. Expansible occluders 10 and 12 are then placed into the right and left common carotid arteries, respectively, and connected brachiocephalic to an extracorporeal oxygenator and pump 70. Expansible occluder 30 (as illustrated in FIG. 8) is introduced to the superior vena cava SVC and also connected to the external oxygenator and pump 70. Blood is introduced to the common carotid arteries through the expansible occluders 10 and 12 and return to the external oxygenator and pump through the expansible occluder 30. A reservoir of blood is maintained within the external oxygenator and pump 70 so that sufficient blood will remain in circulation even as a certain amount of blood is lost since it flows outwardly to points other than the superior vena cava.

Preferably, perfusion and oxygenation of the lower portion of the patient P is accomplished using expansible occluders 40 and 50 which are introduced intravascularly according to conventional techniques, such as the Seldinger technique. In this way, the cerebral vasculature and lower body vasculature may be continuously perfused with oxygenated blood while blood is kept out of the aorta and the aorta may be opened for performing a desired procedure.

For open surgical procedures as illustrated in FIG. 10, the patient's heart will be arrested using conventional techniques. Typically, the heart will be catheterized and cooled, and supplied with cardioplegia, according to known techniques. The aorta, typically at the aortic arch, may then be opened and a desired procedure performed. After the procedure is complete, cardioplegia will be stopped-the heart will be warmed, and heart function reestablished.

A particular advantage of the present invention is that the cerebral vasculature may continue to be isolated during the period immediately following cessation of bypass and reestablishment of heart function. It will be appreciated that any procedure performed in and around the aorta may leave significant debris in the aortic lumen presenting a substantial risk of embolization to the patient. By reestablishing heart function and blood flow through the aorta while maintaining isolation of the cerebral vasculature, the potentially embolic material may be cleared from the aorta and removed to less sensitive portions of the vasculature. Blood flow to the cerebral vasculature can then be reestablished, typically from 2 minutes to 5 minutes following the restarting of the heart.

Figure 11:
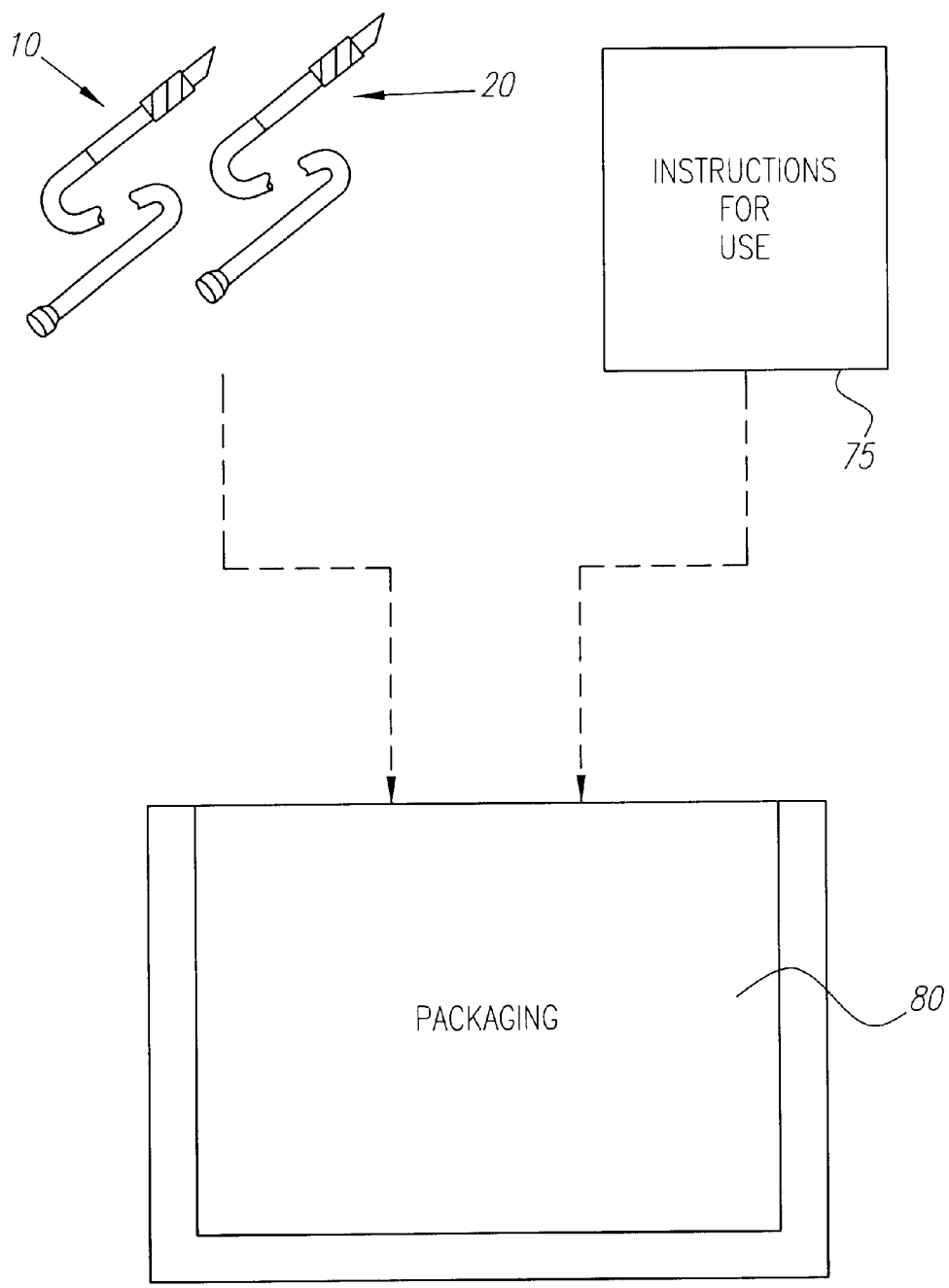
FIG. 11 illustrates a kit constructed in accordance with the principles of the present invention.

Referring now to FIG. 11, kits according to the present invention will comprise at least one expansible occluder 10, usually comprising at least two expansible cannulas 10 and 12, as illustrated, instructions for use (IFU) 75. The expansible occluders 10 and 12 will be suitable for connection to an extracorporeal flow system 70 (FIG. 10), or for connection to a reservoir of oxygenated medium, depending on the intended use. The instructions for use 75 will set forth any of the methods described above. Usually, the expansible occluders 10 and 12 and instructions for use 75 will be packaged together in a suitable package 80, such as a pouch, tray, box, tube, or the like. Optionally, the instructions for use may be printed in whole or in part on a portion of the packaging 80. Usually, at least the expansible occluders 10 and 12 will be sterilely maintained within the package 80. Other optional kit components which could be placed within the package 80 include oxygenated medium, cerebral protective agents and/or other drugs, additional catheters for connecting the cannulas to system 70 or other extracorporeal apparatus, replaceable cassettes for system 70 which permit replacement of all system components which directly contact the blood, and the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for cerebral cooling, comprising the steps of:
providing a catheter having a proximal end, a distal end, and a lumen therebetween, the distal end having a first expandable occlusive member, a second expandable occlusive member, and one or more ports therebetween and communicating with the lumen;

inserting the catheter into a right subclavian artery;

positioning the first expandable occlusive member in the right brachiocephalic artery upstream of the right common carotid artery;

positioning the second expandable occlusive member in the right subclavian artery downstream of the right common carotid artery; and flowing hypothermic medium from the catheter into at least one of the right common carotid artery or the right vertebral artery.

2. The method of claim 1, further comprising the step of stopping blood flow within the aorta.

3. The method of claim 1, further comprising the step of performing a diagnostic or interventional procedure on the aorta.

4. The method of claim 1, further comprising the step of performing an open surgical interventional procedure on the aorta.

5. The method of claim 1, further comprising the step of positioning the second expandable occlusive member in the right subclavian artery downstream of the right vertebral artery.

6. A method for cerebral cooling, comprising the steps of:

inserting a first catheter into a right common carotid artery and expanding an occlusion member disposed about the first catheter;

inserting a second catheter into a left common carotid artery and expanding an occlusion member disposed about the second catheter;

inserting a third catheter into a descending aorta and expanding an occlusion member disposed about the third catheter;

inserting a fourth catheter into an inferior vena cava and expanding an occlusion member disposed about the fourth catheter;

flowing oxygenated medium from the first catheter into the right common carotid artery;

flowing oxygenated medium from the second catheter into the left common carotid artery;

flowing oxygenated medium from the third catheter into the descending aorta; and withdrawing medium from the inferior vena cava.

7. The method of claim 6, further comprising the step of stopping blood flow within the aorta.

8. The method of claim 6, further comprising the step of performing a diagnostic or interventional procedure on the aorta.

9. The method of claim 6, further comprising the step of performing an open surgical interventional procedure on the aorta.

10. The method of claim 6, further comprising the step of performing repair of an aortic aneurysm, repair of an aortic dissection, reconstruction of the aorta, or endarterectomy.

* * * * *